(12) United States Patent
Hamprecht et al.

(10) Patent No.: US 6,420,314 B1
(45) Date of Patent: Jul. 16, 2002

(54) SUBSTITUTED 2-PHENYL PYRIDINES, THEIR MANUFACTURE AND USE AS HERBICIDES

(75) Inventors: Gerhard Hamprecht, Weinheim; Peter Schäfer, Ottersheim; Markus Menges, Bensheim; Olaf Menke, Altleiningen; Robert Reinhard; Cyrill Zagar, both of Ludwigshafen; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,971

(22) PCT Filed: May 15, 1998

(86) PCT No.: PCT/EP98/02878

§ 371 (c)(1),
(2), (4) Date: Nov. 17, 1999

(87) PCT Pub. No.: WO98/54137

PCT Pub. Date: Dec. 3, 1998

(30) Foreign Application Priority Data

May 30, 1997 (DE) .......................................... 197 22 660

(51) Int. Cl.[7] .......................... A01N 43/40; C07D 213/70
(52) U.S. Cl. ........................ 504/244; 546/295; 546/288; 546/339; 546/341; 546/342; 546/345; 504/116; 504/167; 504/254
(58) Field of Search ................................ 504/116, 167, 504/244, 254; 546/286, 287, 295, 339, 341, 342, 345

(56) References Cited

U.S. PATENT DOCUMENTS 6,169,184 B1 * 1/2001 Hamprecht et al. ......... 546/345

FOREIGN PATENT DOCUMENTS

| CA | 2230172 | 3/1997 |
| WO | 95/02580 | 1/1995 |
| WO | 95/02590 | 1/1995 |
| WO | 97/08147 | 3/1997 |
| WO | 97/11059 | 3/1997 |

OTHER PUBLICATIONS

U.S. Ser. No. 09/011,610 (OZ 0050/46112).
Drug Design and Delivery, 1989, vol. 4, pp 121–127, Phillips et al.

* cited by examiner

*Primary Examiner*—Charanjit S. Aulakh
(74) *Attorney, Agent, or Firm*—Keil & Weinkauf

(57) ABSTRACT

Substituted 2-phenylpyridines of the formula I

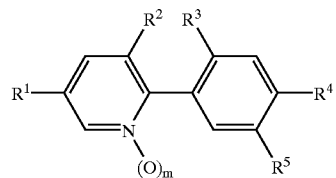

in which the substituents and the index m are defined in the specification.

9 Claims, No Drawings

SUBSTITUTED 2-PHENYL PYRIDINES, THEIR MANUFACTURE AND USE AS HERBICIDES

This application is a 371 of PCT/EP98/02878 filed May 15, 1998, now WO 98/54137 Dec. 3, 1998.

The present invention relates to novel substituted 2-phenylpyridines of the formula I

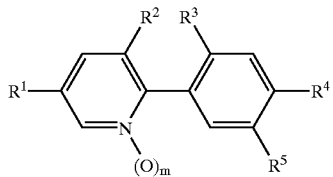

in which the substituents and the index m have the following meanings:

m is 0 or 1;
is halogen, $C_1$–$C_4$-haloalkyl, $C_1$–$C_4$-haloalkoxy, $C_1$–$C_4$-alkylthio, $C_1$–$C_4$-alkylsulfinyl, $C_1$–$C_4$-alkylsulfonyl, $C_1$–$C_4$-haloalkylthio or cyano;
$R^2$ is fluorine or trifluoromethyl;
$R^3$ is hydrogen or halogen;
$R^4$ is halogen or cyano;
$R^5$ is $CO_2R^6$, $OR^7$, $SR^7$, $C(R^8)$=N—O—$R^7$ or $C(R^8)$=C($R^8$)—CO—O—$R^6$, where
  $R^6$ is hydrogen, an unsubstituted or halogen-substituted $C_1$–$C_8$-alkyl-, $C_3$–$C_6$-alkenyl- or $C_3$–$C_6$-alkynyl radical; $C_1$–$C_4$-alkoxy-$C_1$–$C_4$-alkyl, $C_1$–$C_6$-alkoxycarbonyl-$C_1$–$C_4$-alkyl, $C_3$–$C_4$-alkenyloxycarbonyl-$C_1$–$C_4$-alkyl, $C_3$–$C_4$-alkynyloxycarbonyl-$C_1$–$C_4$-alkyl or $C_1$–$C_4$-alkoxy-($C_1$–$C_4$-alkoxy)carbonyl-$C_1$–$C_4$-alkyl;
  $R^7$ may have the meaning of $R^6$ or may be $CH_2$—$CO_2$[$C_1$–$C_4$-alkylene)]—$CO_2R^9$ or $CH[C_1$–$C_4$-alkyl]$CO_2$—[$C_1$–$C_4$-alkylene]—$CO_2R^9$;
  $R^8$ is hydrogen, halogen or $C_1$–$C_4$-alkyl and
  $R^9$ is hydrogen or $C_1$–$C_4$-alkyl,
and the agriculturally useful salts of the compounds I.
Furthermore, the invention relates to
a process for preparing the compounds I and intermediates of the formula II,
herbicides and compositions for the desiccation and/or defoliation of plants which comprise the compounds I as active substances,
methods for controlling undesirable vegetation and for the desiccation and/or defoliation of plants using the compounds I.

Substituted 2-phenyl-3-chloropyridines having herbicidal activity are already known from WO 95/02580, WO 95/02590 and WO 97/11059.

However, the herbicidal activity of the prior art compounds with respect to harmful plants is not always entirely satisfactory.

It is an object of the present invention to provide novel herbicidally active compounds which allow better selective control of undesirable plants. It is a further object to provide novel compounds which have desiccant/defoliant action.

We have found that these objects are achieved by the substituted 2-phenylpyridines of the formula I defined at the outset having herbicidal activity, and by the novel intermediates II for their preparation.

Depending on the substitution pattern, the compounds of the formula I can contain one or more chiral centers, in which case they exist in the form of enantiomer or diastereomer mixtures. The invention relates to the pure enantiomers or diastereomers and also to mixtures thereof.

The substituted 2-phenylpyridines I where $R^6$, $R^7$ and $R^9$=hydrogen may be present in the form of their agriculturally useful salts, the kind of salts usually not being important. Suitable in general are the salts of those bases whose herbicidal activity is not impaired in comparison to the free compound I.

Suitable salts are in particular those of the alkali metals, preferably sodium salts and potassium salts, of the alkaline earth metals, preferably calcium salts and magnesium salts, those of the transition metals, preferably zinc salts and iron salts, and ammonium salts where the ammonium ion, if desired, may carry one to four $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)ammonium salts, furthermore phosphonium salts, sulfonium salts such as preferably tri-($C_1$–$C_4$-alkyl)sulfonium salts and sulfoxonium salts such as preferably tri-($C_1$–$C_4$-alkyl)sulfoxonium salts.

The terms alkyl, alkylene haloalkyl, alkoxy, carboxyalkyl, alkoxyalkyl, alkoxycarbonylalkyl, alkenyl and alkynyl used in the definition of the substituents $R^1$, $R^6$, $R^7$, $R^8$ and $R^9$ are—like the term halogen—collective terms for individual enumerations of the individual group members. All alkyl moieties may be straight-chain or branched. The haloalkyl radical preferably carries one to five identical or different halogen atoms.

Specific meanings are, for example:
halogen: fluorine, chlorine, bromine and iodine, preferably fluorine and chlorine;
$C_1$–$C_4$-alkyl: methyl, ethyl, n-propyl, 1-methylethyl, n-butyl, 1-methylpropyl, 2-methylpropyl and 1,1-dimethylethyl;
$C_1$–$C_6$-alkyl: $C_1$–$C_4$-alkyl as mentioned above, and n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
$C_1$–$C_8$-alkyl: $C_1$–$C_6$-alkyl as mentioned above, and, inter alia, n-heptyl, n-octyl;
$C_3$–$C_4$-alkenyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl;
$C_3$–$C_6$-alkenyl: $C_3$–$C_4$-alkenyl as mentioned above, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably ethenyl and prop-2-en-1-yl;

$C_3$–$C_4$-alkynyl: prop-1-in-1-yl, prop-2-in-3-yl, n-but-1-in-1-yl, n-but-1-in-4-yl, n-but-2-in-1-yl;

$C_3$–$C_6$-alkynyl: $C_3$–$C_4$-alkynyl as mentioned above, and n-pent-1-in-1-yl, n-pent-1-in-3-yl, n-pent-1-in-4-yl, n-pent-1-in-5-yl, n-pent-2-in-1-yl, n-pent-2-in-4-yl, n-pent-2-in-5-yl, 3-methylbut-1-in-1-yl, 3-methylbut-1-in-3-yl, 3-methylbut-1-in-4-yl, n-hex-1-in-1-yl, n-hex-1-in-3-yl, n-hex-1-in-4-yl, n-hex-1-in-5-yl, n-hex-1-in-6-yl, n-hex-2-in-1-yl, n-hex-2-in-4-yl, n-hex-2-in-5-yl, n-hex-2-in-6-yl, n-hex-3-in-1-yl, n-hex-3-in-2-yl, 3-methylpent-1-in-1-yl, 3-methylpent-1-in-3-yl, 3-methylpent-1-in-4-yl, 3-methylpent-1-in-5-yl, 4-methylpent-1-in-1-yl, 4-methylpent-2-in-4-yl and 4-methylpent-2-in-5-yl, preferably prop-2-in-1-yl, 1-methylprop-2-in-1-yl;

$C_1$–$C_3$-fluoroalkyl: $C_1$–$C_3$-alkyl as mentioned above where in each case 1–5 hydrogen atoms are replaced by fluorine, e.g. fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoropropyl, preference is given to difluoromethyl, trifluoromethyl, 2,2,2-trifluoroethyl, pentafluoroethyl and 3,3,3-trifluoropropyl, particular preference is given to trifluoromethyl;

$C_1$–$C_4$-haloalkyl: $C_1$–$C_4$-alkyl as mentioned above which is partially or fully substituted by fluorine, chlorine and/or bromine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_1$–$C_4$-haloalkoxy: $C_1$–$C_4$-alkoxy as mentioned above which is partially or fully substituted by fluorine, chlorine and/or bromine, i.e. for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably $C_1$–$C_2$-haloalkoxy such as trifluoromethoxy;

$C_1$–$C_4$-alkylthio: methylthio, ethylthio, n-propylthio, 1-methylethylthio, n-butylthio, 1-methylpropylthio, 2-methylpropylthio and 1,1-dimethylethylthio, preferably methylthio, ethylthio, methylethylthio;

$C_1$–$C_4$-haloalkylthio: chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio, preferably $C_1$–$C_2$-haloalkylthio such as trifluoromethylthio;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl;

$C_1$–$C_4$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl;

$C_1$–$C_4$-alkoxy-$C_1$–$C_4$-alkyl: $C_1$–$C_4$-alkyl which is substituted by $C_1$–$C_4$-alkoxy such as methoxy, ethoxy, n-propoxy, 1-methylethoxy, n-butoxy, 1-methylpropoxy, 2-methylpropoxy and 1,1-dimethylethoxy, i.e. for example $CH_2OCH_3$, $CH_2OC_2H_5$, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably n-propoxymethyl, (1-methylethoxy)methyl, 2-(n-propoxy)ethyl and 2-(1-methylethoxy)ethyl and particularly preferably $CH_2OCH_3$, $CH_2OC_2H_5$, 2-methoxyethyl or 2-ethoxyethyl;

($C_1$–$C_6$-alkoxy)carbonyl-$C_1$–$C_2$-alkyl: $C_1$–$C_4$-alkyl which is substituted by ($C_1$–$C_6$-alkoxy)carbonyl such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl, $COOC(CH_3)_3$, n-pentoxycarbonyl, 1-methylbutoxycarbonyl and n-hexoxycarbonyl, i.e. for example $CH_2$—$COOCH_3$, $CH_2$—$COOC_2H_5$, n-propoxycarbonylmethyl, $CH_2$—$COOCH(CH_3)_2$, n-butoxycarbonylmethyl, (1-methylpropoxycarbonyl)methyl, (2-methylpropoxycarbonyl)methyl, $CH_2$—$COOC(CH_3)_3$, n-pentoxycarbonylmethyl, (1-methylbutoxycarbonyl)-methyl, n-Hexoxycarbonylmethyl, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 1-(n-pentoxycarbonyl)ethyl, 1-(1-methylbutoxycarbonyl)ethyl, 1-(n-hexoxycarbonyl)ethyl, 2-(methoxycarbonyl)ethyl, 1-(n-hexoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl;

($C_1$–$C_6$-alkoxy)carbonyl-$C_1$–$C_4$-alkyl: ($C_1$–$C_6$-alkoxy)carbonyl-$C_1$–$C_2$-alkyl as mentioned above, and 2-(methoxycarbonyl)propyl, 2-(ethoxycarbonyl)propyl, 2-(n-propoxycarbonyl)propyl, 2-(1-methylethoxycarbonyl)propyl, 2-(n-butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl)propyl, 3-(ethoxycarbonyl)propyl, 3-(n-propoxycarbonyl)propyl, 3-(1-methylethoxycarbonyl)propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(n-propoxycarbonyl)butyl, 2-(1-methylethoxycarbonyl)butyl, 2-(n-butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(n-propoxycarbonyl)butyl, 3-(1-methylethoxycarbonyl)butyl, 3-(n-butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)butyl, 4-(ethoxycarbonyl)butyl, 4-(n-propoxycarbonyl)butyl, 4-(1-methylethoxycarbonyl)butyl, 4-(n-butoxycarbonyl)butyl, 4-(1-methylpropoxycarbonyl)butyl, 4-(2-methylpropoxycarbonyl)butyl or 4-(1,1-dimethylethoxycarbonyl)butyl, preferably $CH_2$—$COOCH_3$, $CH_2$—$COOC_2H_5$, 1-(methoxycarbonyl)ethyl or 1-(ethoxycarbonyl)ethyl;

$C_1$–$C_3$-alkoxy-($C_1$–$C_3$-alkoxy)carbonyl-$C_1$–$C_2$-alkyl: ($C_1$–$C_3$-alkoxy)carbonyl-$C_1$–$C_2$-alkyl such as $CH_2COOCH_3$, $CH_2COOC_2H_5$, $CH_2COOCH_2$—$C_2H_5$, $CH_2COOCH(CH_3)_2$, $CH(CH_3)COOCH_3$, $CH(CH_3)COOC_2H_5$, $CH_2CH_2COOCH_3$, $CH_2CH_2COOC_2H_5$, $CH_2CH_2COOCH_2$—$C_2H_5$, $CH_2CH_2COOCH(CH_3)_2$, 2-($COOCH_3$)propyl, 2-($COOC_2H_5$)propyl, 2-($COOCH_2$—$C_2H_5$)propyl, 2-[$COOCH(CH_3)_2$]propyl, 3-($COOCH_3$)propyl, 3-($COOC_2H_5$)propyl, 3-($COOCH_2$—$C_2H_5$)propyl, 3-[$COOCH(CH_3)_2$]propyl, preferably $CH_2COOCH_3$ or $CH_2COOC_2H_5$, which is substituted in the $C_1$–$C_3$-alkoxy moiety by $OCH_3$, $OC_2H_5$, $OCH_2$—$C_2H_5$ or $OCH(CH_3)_2$, i.e. for example $CH_2COOCH_2OCH_3$, $CH_2COOCH_2OC_2H_5$, $CH_2COOCH_2OCH(CH_3)_2$ or $CH_2COOCH_2OC(CH_3)_3$;

$C_1$–$C_4$-alkoxy-($C_1$–$C_4$-alkoxy)carbonyl-$C_1$–$C_4$-alkyl: $C_1$–$C_3$-alkoxy-($C_1$–$C_3$-alkoxy)carbonyl-$C_1$–$C_2$-alkyl as mentioned above where one or both of the alkoxy moieties may additionally be n-butoxy, sec-butoxy, iso-butoxy or tert-butoxy, and 2-($COOCH_3$)butyl, 2-($COOC_2H_5$)butyl, 2-($COOCH_2$—$C_2H_5$)butyl, 2-[$COOCH(CH_3)_2$]butyl, 3-($COOCH_3$)butyl, 3-($COOC_2H_5$)butyl, 3-($COOCH_2$—$C_2H_5$)butyl, 3-[$COOCH(CH_3)_2$]butyl, 4-($COOCH_3$)butyl, 4-($COOC_2H_5$)butyl, 4-($COOCH_2$—$C_2H_5$)butyl, 4-[$COOCH(CH_3)_2$]butyl.

$C_1$–$C_4$-alkylene is, for example, methylene, 1,1-ethylene, 1,2-ethylene, 1,1-propylene, 1,2-propylene, 1,3-propylene, 2,2-propylene, 1,1-butylene, 1,2-butylene, 1,3-butylene, 1,4-butylene, 2,2-butylene, 2,3-butylene, 2-methyl-1,1-propylene, 2-methyl-1,2-propylene or 2-methyl-1,3-propylene, preferably methylene, 1,1-ethylene or 2,2-propylene.

With respect to the use of the substituted 2-phenylpyridines I according to the invention as herbicides and/or as desiccants/defoliants, the substituents and the index m preferably have the following meanings, in each case either alone or in combination:

m is 0, $R^1$ is $C_1$–$C_3$-fluoroalkyl, chlorine, methylsulfonyl or cyano;

$R^2$ is fluorine or trifluoromethyl;

$R^3$ is fluorine or chlorine;

$R^4$ is chlorine;

$R^5$ is $CO_2R^6$, $OR^7$ or $SR^7$, where
  $R^6$ is hydrogen, $C_1$–$C_5$-alkyl, $C_3$–$C_4$-alkenyl, 3-chloroprop-2-ene, $C_3$–$C_4$-alkynyl, $C_1$–$C_3$-alkoxy-$C_1$–$C_2$-alkyl, $C_1$–$C_6$-alkoxycarbonyl-$C_1$–$C_2$-alkyl, propargyloxycarbonyl-$C_1$–$C_2$-alkyl, $C_1$–$C_3$-alkoxy-$C_1$–$C_3$-alkoxycarbonyl-$C_1$–$C_2$-alkyl;
  $R^7$ may have the meaning of $R^6$ or may be $CH_2$—$CO_2$[$C_1$–$C_2$-alkylene]—$CO_2R^9$ or $CH[C_1$–$C_2$-alkyl]—$CO_2$—[$C_1$–$C_2$-alkylene]—$CO_2R^9$;
  $R^8$ is hydrogen, halogen or $C_1$–$C_4$-alkyl and
  $R^9$ is hydrogen or $C_1$–$C_4$-alkyl, and the agriculturally useful salts of the compounds I.

Particular preference is given to the substituted 2-phenylpyridines Ia (= where m=0, $R^2$=fluorine and $R^4$=chlorine), in particular to those compounds listed in Table A below:

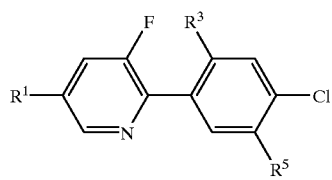

Ia

| No. | $R^1$ | $R^3$ | $R^5$ | mp (° C.), $n^{25}_D$, IR($\gamma$) |
|---|---|---|---|---|
| Ia.1 | $CF_3$ | F | $OCH_3$ | 79–80 |
| Ia.2 | $CF_3$ | F | O—$CH_2$—CH=$CH_2$ | |
| Ia.3 | $CF_3$ | F | O—$CH_2$—CH=CHCl | |
| Ia.4 | $CF_3$ | F | O—$CH_2$—CH=CH—$CH_3$ | |

-continued

| | | | | |
|---|---|---|---|---|
| Ia.5 | CF$_3$ | F | O—CH$_2$—C≡CH | 68–70 |
| Ia.6 | CF$_3$ | F | O—CH$_2$—C≡C—CH$_3$ | |
| Ia.7 | CF$_3$ | F | SCH$_3$ | |
| Ia.8 | CF$_3$ | F | S—CH$_2$—CH=CH$_2$ | |
| Ia.9 | CF$_3$ | F | S—CH$_2$—CH=CHCl | |
| Ia.10 | CF$_3$ | F | S—CH$_2$—CH=CH—CH$_3$ | |
| Ia.11 | CF$_3$ | F | S—CH$_2$—C≡CH | |
| Ia.12 | CF$_3$ | F | S—CH$_2$—C≡C—CH$_3$ | |
| Ia.13 | CF$_3$ | F | CO$_2$CH$_3$ | |
| Ia.14 | CF$_3$ | F | CO$_2$Et | resin, IR: C=O 1753 cm$^{-1}$ |
| Ia.15 | CF$_3$ | F | CO$_2$-n-C$_3$H$_7$ | resin, IR: C=O 1754 cm$^{-1}$ |
| Ia.16 | CF$_3$ | F | CO$_2$-i-C$_3$H$_7$ | |
| Ia.17 | CF$_3$ | F | CO$_2$-n-C$_4$H$_9$ | |
| Ia.18 | CF$_3$ | F | CO$_2$-sec-C$_4$H$_9$ | |
| Ia.19 | CF$_3$ | F | CO$_2$-n-C$_5$H$_{11}$ | |
| Ia.20 | CF$_3$ | F | CO$_2$—CH$_2$—CH=CH$_2$ | |
| Ia.21 | CF$_3$ | F | CO$_2$—CH$_2$—C≡CH | |
| Ia.22 | CF$_3$ | F | CO$_2$—CH$_2$—CH$_2$—O—CH$_3$ | |
| Ia.23 | CF$_3$ | F | CO$_2$—CH$_2$—CH$_2$—O—C$_2$H$_5$ | |
| Ia.24 | CF$_3$ | F | CO$_2$CH$_2$—CH$_2$—O-n-C$_3$H$_7$ | |
| Ia.25 | CF$_3$ | F | CO$_2$—CH$_2$—CO$_2$CH$_3$ | |
| Ia.26 | CF$_3$ | F | CO$_2$—CH$_2$—CO$_2$C$_2$H$_5$ | |
| Ia.27 | CF$_3$ | F | CO$_2$CH$_2$—CO$_2$-n-C$_3$H$_7$ | |
| Ia.28 | CF$_3$ | F | CO$_2$CH$_2$CO$_2$—CH$_2$CH$_2$—OCH$_3$ | |
| Ia.29 | CF$_3$ | F | CO$_2$CH$_2$CO$_2$—CH$_2$CH$_2$—OC$_2$H$_5$ | |
| Ia.30 | CF$_3$ | F | O—CH$_2$CO$_2$CH$_3$ | 65–67 |
| Ia.31 | CF$_3$ | F | O—CH$_2$CO$_2$C$_2$H$_5$ | |
| Ia.32 | CF$_3$ | F | O—CH$_2$CO$_2$-n-C$_3$H$_7$ | |
| Ia.33 | CF$_3$ | F | O—CH$_2$CO$_2$-n-C$_4$H$_9$ | |
| Ia.34 | CF$_3$ | F | O—CH$_2$CO$_2$-sec-C$_4$H$_9$ | |
| Ia.35 | CF$_3$ | F | O—CH$_2$CO$_2$-n-C$_5$H$_{11}$ | |
| Ia.36 | CF$_3$ | F | S—CH$_2$CO$_2$CH$_3$ | |
| Ia.37 | CF$_3$ | F | S—CH$_2$CO$_2$C$_2$H$_5$ | |
| Ia.38 | CF$_3$ | F | S—CH$_2$CO$_2$-n-C$_3$H$_7$ | |
| Ia.39 | CF$_3$ | F | S—CH$_2$CO$_2$-n-C$_4$H$_9$ | |
| Ia.40 | CF$_3$ | F | S—CH$_2$CO$_2$-sec-C$_4$H$_9$ | |
| Ia.41 | CF$_3$ | F | S—CH$_2$CO$_2$-n-C$_5$H$_{11}$ | |
| Ia.42 | CF$_3$ | F | O—CH$_2$—CO$_2$—CH$_2$CO$_2$CH$_3$ | |
| Ia.43 | CF$_3$ | F | O—CH$_2$—CO$_2$—CH$_2$CO$_2$C$_2$H$_5$ | |
| Ia.44 | CF$_3$ | F | O—CH(CH$_3$)CO$_2$—CH$_2$CO$_2$CH$_3$ | |
| Ia.45 | CF$_3$ | F | O—CH(CH$_3$)CO$_2$—CH$_2$CO$_2$C$_2$H$_5$ | |
| Ia.46 | CF$_3$ | F | S—CH$_2$—CO$_2$—CH$_2$CO$_2$CH$_3$ | |
| Ia.47 | CF$_3$ | F | S—CH$_2$—CO$_2$CH$_2$CO$_2$C$_2$H$_5$ | |
| Ia.48 | CF$_3$ | F | S—CH(CH$_3$)—CO$_2$—CH$_2$CO$_2$CH$_3$ | |
| Ia.49 | CF$_3$ | F | S—CH(CH$_3$)—CO$_2$—CH$_2$CO$_2$C$_2$H$_5$ | |
| Ia.50 | CF$_3$ | F | O—CH$_2$CH$_2$—CH$_2$CH$_2$—OCH$_3$ | |
| Ia.51 | CF$_3$ | F | O—CH$_2$CO$_2$—CH$_2$CH$_2$—OC$_2$H$_5$ | |
| Ia.52 | CF$_3$ | F | S—CH$_2$CO$_2$—CH$_2$CH$_2$—OCH$_3$ | |
| Ia.53 | CF$_3$ | F | S—CH$_2$CO$_2$—CH$_2$CH$_2$—OC$_2$H$_5$ | |
| Ia.54 | CF$_3$ | F | O—CH(CH$_3$)—CO$_2$CH$_3$ R enantiomer | resin, see Example 8 |
| Ia.55 | CF$_3$ | F | O—CH(CH$_3$)—CO$_2$C$_2$H$_5$ | |
| Ia.56 | CF$_3$ | F | O—CH(CH$_3$)—CO$_2$n-C$_3$H$_7$ | |
| Ia.57 | CF$_3$ | F | S—CH(CH$_3$)—CO$_2$—CH$_3$ | |
| Ia.58 | CF$_3$ | F | S—CH(CH$_3$)—CO$_2$C$_2$H$_5$ | |
| Ia.59 | CF$_3$ | F | S—CH(CH$_3$)—CO$_2$-n-C$_3$H$_7$ | |
| Ia.60 | CF$_3$ | F | O—CH(CH$_3$)—CO$_2$—CH$_2$CH$_2$—OCH$_3$ R enantiomer | $n^{23}_D$ = 1.5115 |
| Ia.61 | CF$_3$ | F | O—CH(CH$_3$)—CO$_2$—CH$_2$CH$_2$—OC$_2$H$_5$ R enantiomer | resin, IR: C=O 1755 cm$^{-1}$ |
| Ia. 62 | CF$_3$ | F | O—CH(CH$_3$)—CO$_2$—CH$_2$CH$_2$—O-n-C$_3$H$_7$ R enantiomer | |
| Ia.63 | Cl | F | OCH$_3$ | 120–122 |
| Ia.64 | Cl | F | O—CH$_2$—CH=CH$_2$ | |
| Ia.65 | Cl | F | O—CH$_2$—CH=CHCl | |
| Ia.66 | Cl | F | O—CH$_2$—CH=CH—CH$_3$ | |
| Ia.67 | Cl | F | O—CH$_2$—C≡CH | 86–87 |
| Ia.68 | Cl | F | O—CH$_2$—C≡C—CH$_3$ | |
| Ia.69 | Cl | F | SCH$_3$ | |
| Ia.70 | Cl | F | S—CH$_2$—CH=CH$_2$ | |
| Ia.71 | Cl | F | S—CH$_2$—CH=CHCl | |
| Ia.72 | Cl | F | S—CH$_2$—CH=CH—CH$_3$ | |
| Ia.73 | Cl | F | S—CH$_2$—C≡CH | |
| Ia.74 | Cl | F | S—CH$_2$—C≡C—CH$_3$ | |

-continued

| ID | | | | |
|---|---|---|---|---|
| Ia.75 | Cl | F | CO₂CH₃ | |
| Ia.76 | Cl | F | CO₂Et | |
| Ia.77 | Cl | F | CO₂-n-C₃H₇ | |
| Ia.78 | Cl | F | CO₂-i-C₃H₇ | |
| Ia.79 | Cl | F | CO₂-n-C₄H₉ | |
| Ia.80 | Cl | F | CO₂-sec-C₄H₉ | |
| Ia.81 | Cl | F | CO₂-n-C₅H₁₁ | |
| Ia.82 | Cl | F | CO₂—CH₂—CH=CH₂ | |
| Ia.83 | Cl | F | CO₂—CH₂—C≡CH | |
| Ia.84 | Cl | F | CO₂—CH₂—CH₂—O—CH₃ | |
| Ia.85 | Cl | F | CO₂—CH₂—CH₂—O—C₂H₅ | |
| Ia.86 | Cl | F | CO₂CH₂—CH₂—O-n-C₃H₇ | |
| Ia.87 | Cl | F | CO₂—CH₂—CO₂CH₃ | |
| Ia.88 | Cl | F | CO₂—CH₂—CO₂C₂H₅ | |
| Ia.89 | Cl | F | CO₂CH₂—CO₂-n-C₃H₇ | |
| Ia.90 | Cl | F | CO₂CH₂CO₂—CH₂CH₂—OCH₃ | |
| Ia.91 | Cl | F | CO₂CH₂CO₂—CH₂CH₂—OC₂H₅ | |
| Ia.92 | Cl | F | O—CH₂CO₂CH₃ | |
| Ia.93 | Cl | F | O—CH₂CO₂C₂H₅ | |
| Ia.94 | Cl | F | O—CH₂CO₂-n-C₃H₇ | |
| Ia.95 | Cl | F | O—CH₂CO₂-n-C₄H₉ | |
| Ia.96 | Cl | F | O—CH₂CO₂-sec-C₄H₉ | |
| Ia.97 | Cl | F | O—CH₂CO₂-n-C₅H₁₁ | |
| Ia.98 | Cl | F | S—CH₂CO₂CH₃ | |
| Ia.99 | Cl | F | S—CH₂CO₂C₂H₅ | |
| Ia.100 | Cl | F | S—CH₂CO₂-n-C₃H₇ | |
| Ia.101 | Cl | F | S—CH₂CO₂-n-C₄H₉ | |
| Ia.102 | Cl | F | S—CH₂CO₂-sec-C₄H₉ | |
| Ia.103 | Cl | F | S—CH₂CO₂-n-C₅H₁₁ | |
| Ia.104 | Cl | F | O—CH₂—CO₂—CH₂CO₂CH₃ | |
| Ia.105 | Cl | F | O—CH₂—CO₂—CH₂CO₂C₂H₅ | |
| Ia.106 | Cl | F | O—CH(CH₃)CO₂—CH₂CO₂CH₃ | |
| Ia.107 | Cl | F | O—CH(CH₃)CO₂—CH₂CO₂C₂H₅ | |
| Ia.108 | Cl | F | S—CH₂—CO₂—CH₂CO₂CH₃ | |
| Ia.109 | Cl | F | S—CH₂—CO₂CH₂CO₂C₂H₅ | |
| Ia.110 | Cl | F | S—CH(CH₃)—CO₂—CH₂CO₂CH₃ | |
| Ia.111 | Cl | F | S—CH(CH₃)—CO₂—CH₂CO₂C₂H₅ | |
| Ia.112 | Cl | F | O—CH₂CH₂—CH₂CH₂—OCH₃ | |
| Ia.113 | Cl | F | O—CH₂CO₂—CH₂CH₂—OC₂H₅ | |
| Ia.114 | Cl | F | S—CH₂CO₂—CH₂CH₂—OCH₃ | |
| Ia.115 | Cl | F | S—CH₂CO₂—CH₂CH₂—OC₂H₅ | |
| Ia.116 | Cl | F | O—CH(CH₃)—CO₂CH₃ R enantiomer | 40–42 |
| Ia.117 | Cl | F | O—CH(CH₃)—CO₂C₂H₅ | |
| Ia.118 | Cl | F | O—CH(CH₃)—CO₂-n-C₃H₇ | |
| Ia.119 | Cl | F | S—CH(CH₃)—CO₂—CH₃ | |
| Ia.120 | Cl | F | S—CH(CH₃)—CO₂C₂H₅ | |
| Ia.121 | Cl | F | S—CH(CH₃)—CO₂-n-C₃H₇ | |
| Ia.122 | Cl | F | O—CH(CH₃)—CO₂—CH₂CH₂—OCH₃ | |
| Ia.123 | Cl | F | O—CH(CH₃)—CO₂—CH₂CH₂—OC₂H₅ R enantiomer | IR: C=O 1755 cm⁻¹ |
| Ia.124 | Cl | F | O—CH(CH₃)—CO₂—CH₂CH₂—O-n-C₃H₇ | |
| Ia.125 | CH₃SO₂ | F | OCH₃ | |
| Ia.126 | CH₃SO₂ | F | O—CH₂—CH=CH₂ | |
| Ia.127 | CH₃SO₂ | F | O—CH₂—CH=CHCl | |
| Ia.128 | CH₃SO₂ | F | O—CH₂—CH=CH—CH₃ | |
| Ia.129 | CH₃SO₂ | F | O—CH₂—C≡CH | |
| Ia.130 | CH₃SO₂ | F | O—CH₂—C≡C—CH₃ | |
| Ia.131 | CH₃SO₂ | F | SCH₃ | |
| Ia.132 | CH₃SO₂ | F | S—CH₂—CH=CH₂ | |
| Ia.133 | CH₃SO₂ | F | S—CH₂—CH=CHCl | |
| Ia.134 | CH₃SO₂ | F | S—CH₂—CH=CH—CH₃ | |
| Ia.135 | CH₃SO₂ | F | S—CH₂—C≡CH | |
| Ia.136 | CH₃SO₂ | F | S—CH₂—C≡C—CH₃ | |
| Ia.137 | CH₃SO₂ | F | CO₂CH₃ | |
| Ia.138 | CH₃SO₂ | F | CO₂Et | |
| Ia.139 | CH₃SO₂ | F | CO₂-n-C₃H₇ | |
| Ia.140 | CH₃SO₂ | F | CO₂-i-C₃H₇ | |
| Ia.141 | CH₃SO₂ | F | CO₂-n-C₄H₉ | |
| Ia.142 | CH₃SO₂ | F | CO₂-sec-C₄H₉ | |
| Ia.143 | CH₃SO₂ | F | CO₂-n-C₅H₁₁ | |
| Ia.144 | CH₃SO₂ | F | CO₂—CH₂—CH=CH₂ | |
| Ia.145 | CH₃SO₂ | F | CO₂—CH₂—C≡CH | |
| Ia.146 | CH₃SO₂ | F | CO₂—CH₂—CH₂—O—CH₃ | |
| Ia.147 | CH₃SO₂ | F | CO₂—CH₂—CH₂—O—C₂H₅ | |
| Ia.148 | CH₃SO₂ | F | CO₂CH₂—CH₂—O-n-C₃H₇ | |
| Ia.149 | CH₃SO₂ | F | CO₂—CH₂—CO₂CH₃ | |
| Ia.150 | CH₃SO₂ | F | CO₂—CH₂—CO₂C₂H₅ | |
| Ia.151 | CH₃SO₂ | F | CO₂CH₂—CO₂-n-C₃H₇ | |
| Ia.152 | CH₃SO₂ | F | CO₂CH₂CO₂—CH₂CH₂—OCH₃ | |

-continued

| | | | |
|---|---|---|---|
| Ia.153 | CH$_3$SO$_2$ | F | CO$_2$CH$_2$CO$_2$—CH$_2$CH$_2$—OC$_2$H$_5$ |
| Ia.154 | CH$_3$SO$_2$ | F | O—CH$_2$CO$_2$CH$_3$ |
| Ia.155 | CH$_3$SO$_2$ | F | O—CH$_2$CO$_2$C$_2$H$_5$ |
| Ia.156 | CH$_3$SO$_2$ | F | O—CH$_2$CO$_2$-n-C$_3$H$_7$ |
| Ia.157 | CH$_3$SO$_2$ | F | O—CH$_2$CO$_2$-n-C$_4$H$_9$ |
| Ia.158 | CH$_3$SO$_2$ | F | O—CH$_2$CO$_2$-sec-C$_4$H$_9$ |
| Ia.159 | CH$_3$SO$_2$ | F | O—CH$_2$CO$_2$-n-C$_5$H$_{11}$ |
| Ia.160 | CH$_3$SO$_2$ | F | S—CH$_2$CO$_2$CH$_3$ |
| Ia.161 | CH$_3$SO$_2$ | F | S—CH$_2$CO$_2$C$_2$H$_5$ |
| Ia.162 | CH$_3$SO$_2$ | F | S—CH$_2$CO$_2$-n-C$_3$H$_7$ |
| Ia.163 | CH$_3$SO$_2$ | F | S—CH$_2$CO$_2$-n-C$_4$H$_9$ |
| Ia.164 | CH$_3$SO$_2$ | F | S—CH$_2$CO$_2$-sec-C$_4$H$_9$ |
| Ia.165 | CH$_3$SO$_2$ | F | S—CH$_2$CO$_2$-n-C$_5$H$_{11}$ |
| Ia.166 | CH$_3$SO$_2$ | F | O—CH$_2$—CO$_2$—CH$_2$CO$_2$CH$_3$ |
| Ia.167 | CH$_3$SO$_2$ | F | O—CH$_2$—CO$_2$—CH$_2$CO$_2$C$_2$H$_5$ |
| Ia.168 | CH$_3$SO$_2$ | F | O—CH(CH$_3$)CO$_2$—CH$_2$CO$_2$CH$_3$ |
| Ia.169 | CH$_3$SO$_2$ | F | O—CH(CH$_3$)CO$_2$—CH$_2$CO$_2$C$_2$H$_5$ |
| Ia.170 | CH$_3$SO$_2$ | F | S—CH$_2$—CO$_2$—CH$_2$CO$_2$CH$_3$ |
| Ia.171 | CH$_3$SO$_2$ | F | S—CH$_2$—CO$_2$CH$_2$CO$_2$C$_2$H$_5$ |
| Ia.172 | CH$_3$SO$_2$ | F | S—CH(CH$_3$)—CO$_2$—CH$_2$CO$_2$CH$_3$ |
| Ia.173 | CH$_3$SO$_2$ | F | S—CH(CH$_3$)—CO$_2$—CH$_2$CO$_2$C$_2$H$_5$ |
| Ia.174 | CH$_3$SO$_2$ | F | O—CH$_2$CH$_2$—CH$_2$CH$_2$—OCH$_3$ |
| Ia.175 | CH$_3$SO$_2$ | F | O—CH$_2$CO$_2$—CH$_2$CH$_2$—OC$_2$H$_5$ |
| Ia.176 | CH$_3$SO$_2$ | F | S—CH$_2$CO$_2$—CH$_2$CH$_2$—OCH$_3$ |
| Ia.177 | CH$_3$SO$_2$ | F | S—CH$_2$CO$_2$—CH$_2$CH$_2$—OC$_2$H$_5$ |
| Ia.178 | CH$_3$SO$_2$ | F | O—CH(CH$_3$)—CO$_2$CH$_3$ |
| Ia.179 | CH$_3$SO$_2$ | F | O—CH(CH$_3$)—CO$_2$C$_2$H$_5$ |
| Ia.180 | CH$_3$SO$_2$ | F | O—CH(CH$_3$)—CO$_2$-n-C$_3$H$_7$ |
| Ia.181 | CH$_3$SO$_2$ | F | S—CH(CH$_3$)—CO$_2$—CH$_3$ |
| Ia.182 | CH$_3$SO$_2$ | F | S—CH(CH$_3$)—CO$_2$C$_2$H$_5$ |
| Ia.183 | CH$_3$SO$_2$ | F | S—CH(CH$_3$)—CO$_2$-n-C$_3$H$_7$ |
| Ia.184 | CH$_3$SO$_2$ | F | O—CH(CH$_3$)—CO$_2$—CH$_2$CH$_2$—OCH$_3$ |
| Ia.185 | CH$_3$SO$_2$ | F | O—CH(CH$_3$)—CO$_2$—CH$_2$CH$_2$—OC$_2$H$_5$ |
| Ia.186 | CH$_3$SO$_2$ | F | O—CH(CH$_3$)—CO$_2$—CH$_2$CH$_2$—O-n-C$_3$H$_7$ |
| Ia.187 | CN | F | OCH$_3$ |
| Ia.188 | CN | F | O—CH$_2$—CH=CH$_2$ |
| Ia.189 | CN | F | O—CH$_2$—CH=CHCl |
| Ia.190 | CN | F | O—CH$_2$—CH=CH—CH$_3$ |
| Ia.191 | CN | F | O—CH$_2$—C≡CH |
| Ia.192 | CN | F | O—CH$_2$—C≡C—CH$_3$ |
| Ia.193 | CN | F | SCH$_3$ |
| Ia.194 | CN | F | S—CH$_2$—CH=CH$_2$ |
| Ia.195 | CN | F | S—CH$_2$—CH=CHCl |
| Ia.196 | CN | F | S—CH$_2$—CH=CH—CH$_3$ |
| Ia.197 | CN | F | S—CH$_2$—C≡CH |
| Ia.198 | CN | F | S—CH$_2$—C≡C—CH$_3$ |
| Ia.199 | CN | F | CO$_2$CH$_3$ |
| Ia.200 | CN | F | CO$_2$Et |
| Ia.201 | CN | F | CO$_2$-n-C$_3$H$_7$ |
| Ia.202 | CN | F | CO$_2$-i-C$_3$H$_7$ |
| Ia.203 | CN | F | CO$_2$-n-C$_4$H$_9$ |
| Ia.204 | CN | F | CO$_2$-sec-C$_4$H$_9$ |
| Ia.205 | CN | F | CO$_2$-n-C$_5$H$_{11}$ |
| Ia.206 | CN | F | CO$_2$—CH$_2$—CH=CH$_2$ |
| Ia.207 | CN | F | CO$_2$—CH$_2$—C≡CH |
| Ia.208 | CN | F | CO$_2$—CH$_2$—CH$_2$—O—CH$_3$ |
| Ia.209 | CN | F | CO$_2$—CH$_2$—CH$_2$—O—C$_2$H$_5$ |
| Ia.210 | CN | F | CO$_2$CH$_2$—CH$_2$—O-n-C$_3$H$_7$ |
| Ia.211 | CN | F | CO$_2$—CH$_2$—CO$_2$CH$_3$ |
| Ia.212 | CN | F | CO$_2$—CH$_2$—CO$_2$C$_2$H$_5$ |
| Ia.213 | CN | F | CO$_2$CH$_2$—CO$_2$-n-C$_3$H$_7$ |
| Ia.214 | CN | F | CO$_2$CH$_2$CO$_2$—CH$_2$CH$_2$—OCH$_3$ |
| Ia.215 | CN | F | CO$_2$CH$_2$CO$_2$—CH$_2$CH$_2$—OC$_2$H$_5$ |
| Ia.216 | CN | F | O—CH$_2$CO$_2$CH$_3$ |
| Ia.217 | CN | F | O—CH$_2$CO$_2$C$_2$H$_5$ |
| Ia.218 | CN | F | O—CH$_2$CO$_2$-n-C$_3$H$_7$ |
| Ia.219 | CN | F | O—CH$_2$CO$_2$-n-C$_4$H$_9$ |
| Ia.220 | CN | F | O—CH$_2$CO$_2$-sec-C$_4$H$_9$ |
| Ia.221 | CN | F | O—CH$_2$CO$_2$-n-C$_5$H$_{11}$ |
| Ia.222 | CN | F | S—CH$_2$CO$_2$CH$_3$ |
| Ia.223 | CN | F | S—CH$_2$CO$_2$C$_2$H$_5$ |
| Ia.224 | CN | F | S—CH$_2$CO$_2$-n-C$_3$H$_7$ |
| Ia.225 | CN | F | S—CH$_2$CO$_2$-n-C$_4$H$_9$ |
| Ia.226 | CN | F | S—CH$_2$CO$_2$-sec-C$_4$H$_9$ |
| Ia.227 | CN | F | S—CH$_2$CO$_2$-n-C$_5$H$_{11}$ |
| Ia.228 | CN | F | O—CH$_2$—CO$_2$—CH$_2$CO$_2$CH$_3$ |
| Ia.229 | CN | F | O—CH$_2$—CO$_2$—CH$_2$CO$_2$C$_2$H$_5$ |
| Ia.230 | CN | F | O—CH(CH$_3$)CO$_2$—CH$_2$CO$_2$CH$_3$ |
| Ia.231 | CN | F | O—CH(CH$_3$)CO$_2$—CH$_2$CO$_2$C$_2$H$_5$ |

-continued

| No. | R¹ | R³ | R⁵ |
|---|---|---|---|
| Ia.232 | CN | F | S—CH$_2$—CO$_2$—CH$_2$CO$_2$CH$_3$ |
| Ia.233 | CN | F | S—CH$_2$—CO$_2$CH$_2$CO$_2$C$_2$H$_5$ |
| Ia.234 | CN | F | S—CH(CH$_3$)—CO$_2$—CH$_2$CO$_2$CH$_3$ |
| Ia.235 | CN | F | S—CH(CH$_3$)—CO$_2$—CH$_2$CO$_2$C$_2$H$_5$ |
| Ia.236 | CN | F | O—CH$_2$CH$_2$—CH$_2$CH$_2$—OCH$_3$ |
| Ia.237 | CN | F | O—CH$_2$CO$_2$—CH$_2$CH$_2$—OC$_2$H$_5$ |
| Ia.238 | CN | F | S—CH$_2$CO$_2$—CH$_2$CH$_2$—OCH$_3$ |
| Ia.239 | CN | F | S—CH$_2$CO$_2$—CH$_2$CH$_2$—OC$_2$H$_5$ |
| Ia.240 | CN | F | O—CH(CH$_3$)—CO$_2$CH$_3$ |
| Ia.241 | CN | F | O—CH(CH$_3$)—CO$_2$C$_2$H$_5$ |
| Ia.242 | CN | F | O—CH(CH$_3$)—CO$_2$-n-C$_3$H$_7$ |
| Ia.243 | CN | F | S—CH(CH$_3$)—CO$_2$—CH$_3$ |
| Ia.244 | CN | F | S—CH(CH$_3$)—CO$_2$C$_2$H$_5$ |
| Ia.245 | CN | F | S—CH(CH$_3$)—CO$_2$-n-C$_3$H$_7$ |
| Ia.246 | CN | F | O—CH(CH$_3$)—CO$_2$—CH$_2$CH$_2$—OCH$_3$ |
| Ia.247 | CN | F | O—CH(CH$_3$)—CO$_2$—CH$_2$CH$_2$—OC$_2$H$_5$ |
| Ia.248 | CN | F | O—CH(CH$_3$)—CO$_2$—CH$_2$CH$_2$—O-n-C$_3$H$_7$ |

| No. | R¹ | R³ | R⁵ | mp (° C.), $n^{25}_D$, ¹H NMR; R(CDCL$_3$, δ[ppm]) |
|---|---|---|---|---|
| Ia.249 | CF$_3$ | F | OH | 94–96 |
| Ia.250 | CF$_3$ | F | CO$_2$H | |
| Ia.251 | Cl | F | OH | 146–148 |
| Ia.252 | Cl | F | CO$_2$H | |
| Ia.253 | CH$_3$SO$_2$ | F | OH | |
| Ia.254 | CH$_3$SO$_2$ | F | CO$_2$H | |
| Ia.255 | CN | F | OH | |
| Ia.256 | CN | F | CO$_2$H | |
| Ia.257 | CF$_3$ | F | SH | |
| Ia.258 | Cl | F | SH | |
| Ia.259 | CH$_3$SO$_2$ | F | SH | |
| Ia.260 | CN | F | SH | |
| Ia.261 | CF$_3$ | F | O—CH(CH$_3$)CO$_2$H | 48–50 |
| Ia.262 | Cl | F | O—CH(CH$_3$)CO$_2$H | 95 |
| Ia.263 | CH$_3$SO$_2$ | F | O—CH(CH$_3$)CO$_2$H | |
| Ia.264 | CN | F | O—CH(CH$_3$)CO$_2$H | |
| Ia.265 | CF$_3$ | F | O—CH(CH$_3$)—CO$_2$-i-C$_4$H$_9$ R enantiomer | $n^{23}_D$ = 1.5061 |
| Ia.266 | CF$_3$ | F | O—CH(CH$_3$)—CO$_2$—CH$_2$—C≡CH R enantiomer | resin, see Ex. 12 |
| Ia.267 | CF$_3$ | F | OH | 109–110 |
| Ia.268 | CF$_3$ | F | OCH$_3$ | 86–88 |
| Ia.269 | CF$_3$ | F | O—CH$_2$—C≡CH | 63–64 |
| Ia.270 | CF$_3$ | F | O—CH[CH$_3$]—CO$_2$CH$_3$, R enantiomer | resin, 7.75, 8.8 (Pyr), 7.54 6.92, (Ph), 4.75–4.82 (CH), 1, 7 D(CH$_3$), 3.75 (CH$_3$) |

Furthermore, preference is given to the substituted 2-phenylpyridines Ib (= I where m=0, R²=trifluoromethyl, R⁴=chlorine), in particular to the compounds listed in Table B below:

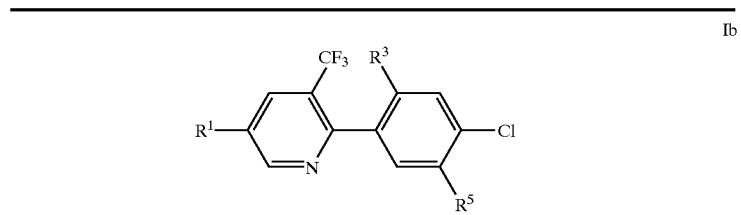

Ib

| No. | R¹ | R³ | R⁵ | mp (° C.), $n^{25}_D$ |
|---|---|---|---|---|
| Ib.1 | CF$_3$ | F | OCH$_3$ | |
| Ib.2 | CF$_3$ | F | O—CH$_2$—CH=CH$_2$ | |
| Ib.3 | CF$_3$ | F | O—CH$_2$—CH=CHCl | |

-continued

| No. | R¹ | R³ | R⁵ |
|---|---|---|---|
| Ib.4 | $CF_3$ | F | $O-CH_2-CH=CH-CH_3$ |
| Ib.5 | $CF_3$ | F | $O-CH_2-C\equiv CH$ |
| Ib.6 | $CF_3$ | F | $O-CH_2-C\equiv C-CH_3$ |
| Ib.7 | $CF_3$ | F | $SCH_3$ |
| Ib.8 | $CF_3$ | F | $S-CH_2-CH=CH_2$ |
| Ib.9 | $CF_3$ | F | $S-CH_2-CH=CHCl$ |
| Ib.10 | $CF_3$ | F | $S-CH_2-CH=CH-CH_3$ |
| Ib.11 | $CF_3$ | F | $S-CH_2-C\equiv CH$ |
| Ib.12 | $CF_3$ | F | $S-CH_2-C\equiv C-CH_3$ |
| Ib.13 | $CF_3$ | F | $CO_2CH_3$ |
| Ib.14 | $CF_3$ | F | $CO_2Et$ |
| Ib.15 | $CF_3$ | F | $CO_2\text{-n-}C_3H_7$ |
| Ib.16 | $CF_3$ | F | $CO_2\text{-i-}C_3H_7$ |
| Ib.17 | $CF_3$ | F | $CO_2\text{-n-}C_4H_9$ |
| Ib.18 | $CF_3$ | F | $CO_2\text{-sec-}C_4H_9$ |
| Ib.19 | $CF_3$ | F | $CO_2\text{-n-}C_5H_{11}$ |
| Ib.20 | $CF_3$ | F | $CO_2-CH_2-CH=CH_2$ |
| Ib.21 | $CF_3$ | F | $CO_2-CH_2-C\equiv CH$ |
| Ib.22 | $CF_3$ | F | $CO_2-CH_2-CH_2-O-CH_3$ |
| Ib.23 | $CF_3$ | F | $CO_2-CH_2-CH_2-O-C_2H_5$ |
| Ib.24 | $CF_3$ | F | $CO_2CH_2-CH_2-O\text{-n-}C_3H_7$ |
| Ib.25 | $CF_3$ | F | $CO_2-CH_2-CO_2CH_3$ |
| Ib.26 | $CF_3$ | F | $CO_2-CH_2-CO_2C_2H_5$ |
| Ib.27 | $CF_3$ | F | $CO_2CH_2-CO_2\text{-n-}C_3H_7$ |
| Ib.28 | $CF_3$ | F | $CO_2CH_2CO_2-CH_2CH_2-OCH_3$ |
| Ib.29 | $CF_3$ | F | $CO_2CH_2CO_2-CH_2CH_2-OC_2H_5$ |
| Ib.30 | $CF_3$ | F | $O-CH_2CO_2CH_3$ |
| Ib.31 | $CF_3$ | F | $O-CH_2CO_2C_2H_5$ |
| Ib.32 | $CF_3$ | F | $O-CH_2CO_2\text{-n-}C_3H_7$ |
| Ib.33 | $CF_3$ | F | $O-CH_2CO_2\text{-n-}C_4H_9$ |
| Ib.34 | $CF_3$ | F | $O-CH_2CO_2\text{-sec-}C_4H_9$ |
| Ib.35 | $CF_3$ | F | $O-CH_2CO_2\text{-n-}C_5H_{11}$ |
| Ib.36 | $CF_3$ | F | $S-CH_2CO_2CH_3$ |
| Ib.37 | $CF_3$ | F | $S-CH_2CO_2C_2H_5$ |
| Ib.38 | $CF_3$ | F | $S-CH_2CO_2\text{-n-}C_3H_7$ |
| Ib.39 | $CF_3$ | F | $S-CH_2CO_2\text{-n-}C_4H_9$ |
| Ib.40 | $CF_3$ | F | $S-CH_2CO_2\text{-sec-}C_4H_9$ |
| Ib.41 | $CF_3$ | F | $S-CH_2CO_2\text{-n-}C_5H_{11}$ |
| Ib.42 | $CF_3$ | F | $O-CH_2-CO_2-CH_2CO_2CH_3$ |
| Ib.43 | $CF_3$ | F | $O-CH_2-CO_2-CH_2CO_2C_2H_5$ |
| Ib.44 | $CF_3$ | F | $O-CH(CH_3)CO_2-CH_2CO_2CH_3$ |
| Ib.45 | $CF_3$ | F | $O-CH(CH_3)CO_2-CH_2CO_2C_2H_5$ |
| Ib.46 | $CF_3$ | F | $S-CH_2-CO_2-CH_2CO_2CH_3$ |
| Ib.47 | $CF_3$ | F | $S-CH_2-CO_2CH_2CO_2C_2H_5$ |
| Ib.48 | $CF_3$ | F | $S-CH(CH_3)-CO_2-CH_2CO_2CH_3$ |
| Ib.49 | $CF_3$ | F | $S-CH(CH_3)-CO_2-CH_2CO_2C_2H_5$ |
| Ib.50 | $CF_3$ | F | $O-CH_2CH_2-CH_2CH_2-OCH_3$ |
| Ib.51 | $CF_3$ | F | $O-CH_2CO_2-CH_2CH_2-OC_2H_5$ |
| Ib.52 | $CF_3$ | F | $S-CH_2CO_2-CH_2CH_2-OCH_3$ |
| Ib.53 | $CF_3$ | F | $S-CH_2CO_2-CH_2CH_2-OC_2H_5$ |
| Ib.54 | $CF_3$ | F | $O-CH(CH_3)-CO_2CH_3$ |

| No. | R¹ | R³ | R⁵ | mp (° C.), $n^{25}_D$, IR(γ), 1H NMR($CDCl_3$ [ppm]) |
|---|---|---|---|---|
| Ib.55 | $CF_3$ | F | $O-CH(CH_3)-CO_2C_2H_5$ | |
| Ib.56 | $CF_3$ | F | $O-CH(CH_3)-CO_2\text{n-}C_3H_7$ | |
| Ib.57 | $CF_3$ | F | $S-CH(CH_3)-CO_2-CH_3$ | |
| Ib.58 | $CF_3$ | F | $S-CH(CH_3)-CO_2C_2H_5$ | |
| Ib.59 | $CF_3$ | F | $S-CH(CH_3)-CO_2\text{-n-}C_3H_7$ | |
| Ib.60 | $CF_3$ | F | $O-CH(CH_3)-CO_2-CH_2CH_2-OCH_3$ | |
| Ib.61 | $CF_3$ | F | $O-CH(CH_3)-CO_2-CH_2CH_2-OC_2H_5$ | |
| Ib.62 | $CF_3$ | F | $O-CH(CH_3)-CO_2-CH_2CH_2-O\text{-n-}C_3H_7$ | |
| Ib.63 | Cl | F | $OCH_3$ | 70–73 |
| Ib.64 | Cl | F | $O-CH_2-CH=CH_2$ | |
| Ib.65 | Cl | F | $O-CH_2-CH=CHCl$ | |
| Ib.66 | Cl | F | $O-CH_2-CH=CH-CH_3$ | |
| Ib.67 | Cl | F | $O-CH_2-C\equiv CH$ | 2.5(CH); 4.75($CH_2$); 7.05, 7.23, 7.75, 8.82 |
| Ib.68 | Cl | F | $O-CH_2-C\equiv C-CH_3$ | |
| Ib.69 | Cl | F | $SCH_3$ | |
| Ib.70 | Cl | F | $S-CH_2-CH=CH_2$ | |
| Ib.71 | Cl | F | $S-CH_2-CH=CHCl$ | |
| Ib.72 | Cl | F | $S-CH_2-CH=CH-CH_3$ | |
| Ib.73 | Cl | F | $S-CH_2-C\equiv CH$ | |

-continued

| No. | $R^1$ | $R^3$ | $R^5$ | mp (° C.), $n^{25}_D$, |
|---|---|---|---|---|
| Ib.74 | Cl | F | S—CH$_2$—C≡C—CH$_3$ | |
| Ib.75 | Cl | F | CO$_2$CH$_3$ | |
| Ib.76 | Cl | F | CO$_2$Et | |
| Ib.77 | Cl | F | CO$_2$-n-C$_3$H$_7$ | |
| Ib.78 | Cl | F | CO$_2$-i-C$_3$H$_7$ | |
| Ib.79 | Cl | F | CO$_2$-n-C$_4$H$_9$ | |
| Ib.80 | Cl | F | CO$_2$-sec-C$_4$H$_9$ | |
| Ib.81 | Cl | F | CO$_2$-n-C$_5$H$_{11}$ | |
| Ib.82 | Cl | F | CO$_2$—CH$_2$—CH=CH$_2$ | |
| Ib.83 | Cl | F | CO$_2$—CH$_2$—C≡CH | |
| Ib.84 | Cl | F | CO$_2$—CH$_2$—CH$_2$—O—CH$_3$ | |
| Ib.85 | Cl | F | CO$_2$—CH$_2$—CH$_2$—O—C$_2$H$_5$ | |
| Ib.86 | Cl | F | CO$_2$CH$_2$—CH$_2$—O-n-C$_3$H$_7$ | |
| Ib.87 | Cl | F | CO$_2$—CH$_2$—CO$_2$CH$_3$ | |
| Ib.88 | Cl | F | CO$_2$—CH$_2$—CO$_2$C$_2$H$_5$ | |
| Ib.89 | Cl | F | CO$_2$CH$_2$—CO$_2$-n-C$_3$H$_7$ | |
| Ib.90 | Cl | F | CO$_2$CH$_2$CO$_2$—CH$_2$CH$_2$—OCH$_3$ | |
| Ib.91 | Cl | F | CO$_2$CH$_2$CO$_2$—CH$_2$CH$_2$—OC$_2$H$_5$ | |
| Ib.92 | Cl | F | O—CH$_2$CO$_2$CH$_3$ | IR: (C=O) 1764 cm$^{-1}$ |
| Ib.93 | Cl | F | O—CH$_2$CO$_2$C$_2$H$_5$ | |
| Ib.94 | Cl | F | O—CH$_2$CO$_2$-n-C$_3$H$_7$ | |
| Ib.95 | Cl | F | O—CH$_2$CO$_2$-n-C$_4$H$_9$ | |
| Ib.96 | Cl | F | O—CH$_2$CO$_2$-sec-C$_4$H$_9$ | |
| Ib.97 | Cl | F | O—CH$_2$CO$_2$-n-C$_5$H$_{11}$ | |
| Ib.98 | Cl | F | S—CH$_2$CO$_2$CH$_3$ | |
| Ib.99 | Cl | F | S—CH$_2$CO$_2$C$_2$H$_5$ | |
| Ib.100 | Cl | F | S—CH$_2$CO$_2$-n-C$_3$H$_7$ | |
| Ib.101 | Cl | F | S—CH$_2$CO$_2$-n-C$_4$H$_9$ | |
| Ib.102 | Cl | F | S—CH$_2$CO$_2$-sec-C$_4$H$_9$ | |
| Ib.103 | Cl | F | S—CH$_2$CO$_2$-n-C$_5$H$_{11}$ | |
| Ib.104 | Cl | F | O—CH$_2$—CO$_2$—CH$_2$CO$_2$CH$_3$ | |
| Ib.105 | Cl | F | O—CH$_2$—CO$_2$—CH$_2$CO$_2$C$_2$H$_5$ | |
| Ib.106 | Cl | F | O—CH(CH$_3$)CO$_2$—CH$_2$CO$_2$CH$_3$ | |
| Ib.107 | Cl | F | O—CH(CH$_3$)CO$_2$—CH$_2$CO$_2$C$_2$H$_5$ | |
| Ib.108 | Cl | F | S—CH$_2$—CO$_2$—CH$_2$CO$_2$CH$_3$ | |
| Ib.109 | Cl | F | S—CH$_2$—CO$_2$CH$_2$CO$_2$C$_2$H$_5$ | |
| Ib.110 | Cl | F | S—CH(CH$_3$)—CO$_2$—CH$_2$CO$_2$CH$_3$ | |
| Ib.111 | Cl | F | S—CH(CH$_3$)—CO$_2$—CH$_2$CO$_2$C$_2$H$_5$ | |
| Ib.112 | Cl | F | O—CH$_2$CH$_2$—CH$_2$CH$_2$—OCH$_3$ | |
| Ib.113 | Cl | F | O—CH$_2$CO$_2$—CH$_2$CH$_2$—OC$_2$H$_5$ | |
| Ib.114 | Cl | F | S—CH$_2$CO$_2$—CH$_2$CH$_2$—OCH$_3$ | |
| Ib.115 | Cl | F | S—CH$_2$CO$_2$—CH$_2$CH$_2$—OC$_2$H$_5$ | |
| Ib.116 | Cl | F | O—CH(CH$_3$)—CO$_2$CH$_3$ R enantiomer | IR: C=O 1760 cm$^{-1}$ |
| Ib.117 | Cl | F | O—CH(CH$_3$)—CO$_2$C$_2$H$_5$ | |
| Ib.118 | Cl | F | O—CH(CH$_3$)—CO$_2$-n-C$_3$H$_7$ | |
| Ib.119 | Cl | F | S—CH(CH$_3$)—CO$_2$—CH$_3$ | |
| Ib.120 | Cl | F | S—CH(CH$_3$)—CO$_2$C$_2$H$_5$ | |
| Ib.121 | Cl | F | S—CH(CH$_3$)—CO$_2$-n-C$_3$H$_7$ | |
| Ib.122 | Cl | F | O—CH(CH$_3$)—CO$_2$—CH$_2$CH$_2$—OCH$_3$ | |
| Ib.123 | Cl | F | O—CH(CH$_3$)—CO$_2$—CH$_2$CH$_2$—OC$_2$H$_5$ | |
| Ib.124 | Cl | F | O—CH(CH$_3$)—CO$_2$—CH$_2$CH$_2$—O-n-C$_3$H$_7$ | |
| Ib.125 | CF$_3$ | F | OH | |
| Ib.126 | CF$_3$ | F | CO$_2$H | |
| Ib.127 | Cl | F | OH | 126–129 |
| Ib.128 | Cl | F | CO$_2$H | |
| Ib.129 | CH$_3$SO$_2$ | F | OH | |
| Ib.130 | CH$_3$SO$_2$ | F | CO$_2$H | |
| Ib.131 | CN | F | OH | |
| Ib.132 | CN | F | CO$_2$H | |
| Ib.133 | CF$_3$ | F | SH | |
| Ib.134 | Cl | F | SH | |
| Ib.135 | CH$_3$SO$_2$ | F | SH | |
| Ib.136 | CN | F | SH | |
| Ib.137 | CF$_3$ | F | O—CH(CH$_3$)CO$_2$H | |
| Ib.138 | Cl | F | O—CH(CH$_3$)CO$_2$H | |
| Ib.139 | CH$_3$SO$_2$ | F | O—CH(CH$_3$)CO$_2$H | |
| Ib.140 | CN | F | O—CH(CH$_3$)CO$_2$H | |
| Ib.141 | CF$_3$ | F | O—CH(CH$_3$)—CO$_2$-i-C$_4$H$_9$ | |
| Ib.142 | CF$_3$ | F | O—CH(CH$_3$)—CO$_2$—CH$_2$—C≡CH | |
| Ib.143 | CF$_3$ | Cl | OH | |
| Ib.144 | CF$_3$ | Cl | OCH$_3$ | |
| Ib.145 | CF$_3$ | Cl | OCH$_2$—C≡CH | |
| Ib.146 | CF$_3$ | Cl | OCH(CH$_3$)—CO$_2$CH$_3$ | |

The substituted 2-phenylpyridines are obtainable by various routes, for example by the processes described in WO 95/02580 and WO 97/11059. The preparation of corresponding 2-phenylpyridine N-oxides of the formula I (m=1) can be carried out by the method of the process described in WO 97/11059. A more recent method of coupling the pyridine and phenyl components, according to which the pyridine sulfoxides IIb and pyridine sulfones IIc are reacted with Grignard or zinc reagents III or IV to give the final products I according to the invention, was described in DE Appl. No. 196 36995.9.

radical with or without substitution by halogen, $C_1$–$C_4$-alkoxy, $C_1$–$C_4$-alkoxycarbonyl, di-($C_1$–$C_4$-alkylamino)carbonyl, cyano or nitro, or is a $C_3$–$C_8$-cycloalkyl radical or a $C_1$–$C_4$-alkylenephenyl, phenyl or naphthyl radical with or without substitution in the phenyl moiety by halogen, $C_1$–$C_3$-alkyl, $C_1$–$C_3$-alkoxy, trifluoromethyl, cyano or nitro.

The terms alkyl, alkenyl, alkynyl, alkylene, alkoxy, alkoxycarbonyl, dialkylaminocarbonyl and cycloalkyl used in the definition of the substituent Z are collective terms for individual enumerations of the individual group members. All alkyl moieties may be straight-chain or branched. The

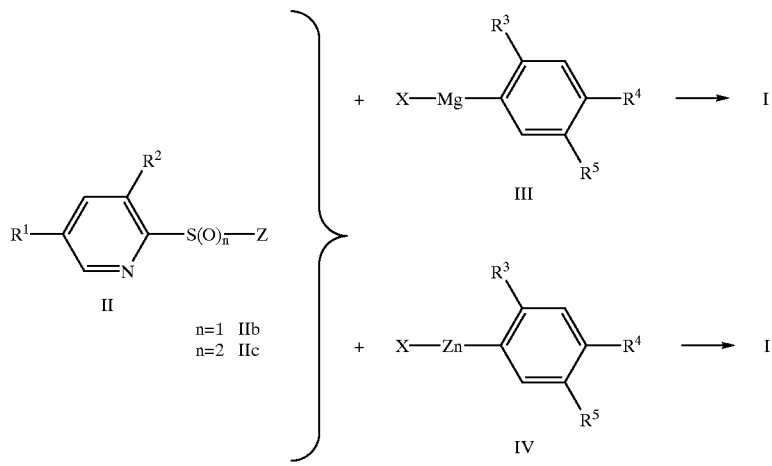

In the formulae III and IV, $R^3$ to $R^5$ are each as defined in claim 1 and X is in each case a halogen atom. The intermediates III and IV and the preparation thereof are described in DE Appl. No. 196 36995.9.

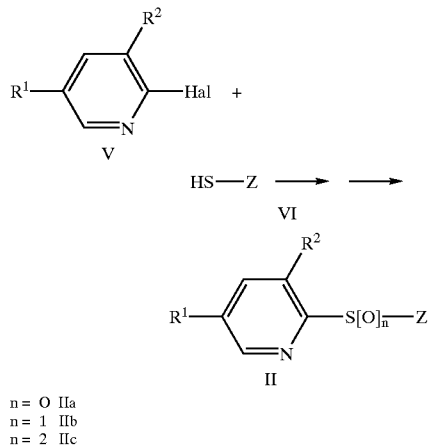

n = 0  IIa
n = 1  IIb
n = 2  IIc

The thiopyridines II can be prepared by the method of the process described in DE Appl. No. 196 36997.5. DE Appl. No. 19722661.2 discloses a particularly favorable route to thiopyridines II starting from 2-halopyridines V and thio compounds of the formula VI in the presence of a copper catalyst.

In the formula II, $R^1$ and $R^2$ are each as defined in claim 1. The pyridine thioethers of the formula IIa (n=0) are starting materials for the preparation of the pyridine sulfoxides IIb (n=1) and pyridine sulfones IIc (n=2); the last two compounds being employed in the coupling reaction with III or IV. Z is a $C_1$–$C_{10}$-alkyl, $C_2$–$C_{10}$-alkenyl or $C_2$–$C_{10}$-alkynyl haloalkyl radical preferably carries one to five identical or different halogen atoms.

Specific examples are:
$C_1$–$C_{10}$-alkyl: $C_1$–$C_8$-alkyl as mentioned in the definition of substituents for $R^6$, and n-nonyl and n-decyl;
1-phenyl with or without substitution by halogen, $C_1$–$C_3$-alkyl, $C_1$–C3-alkoxy, trifluoromethyl, cyano or nitro: 2-, 3-, 4-chlorophenyl, 2-, 3-, 4-tolyl, 2-chloro-4-methylphenyl, 2,4-dichlorophenyl, 2,4,6-trichlorophenyl, 2,6-dichloro-4-methylphenyl, 2-, 3-, 4-methoxyphenyl, 2-chloro-4-methoxyphenyl, 3-chloro-4-methoxyphenyl, 2-, 3-, 4-trifluoromethylphenyl, 2-, 3-, 4-cyanophenyl, 2-, 3-, 4-nitrophenyl, 2-methyl-4-nitrophenyl, 2-chloro-4-trifluoromethylphenyl, 2-chloro-4-nitrophenyl and unsubstituted phenyl.

Particular preference is given to those compounds II in which

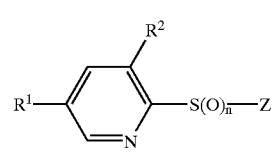

n is 1 or 2;
$R^1$ is trifluoromethyl, chlorine, methylsulfonyl or cyano;
$R^2$ is fluorine or trifluoromethyl and
Z is an unsubstituted or chlorine- or methoxy-substituted $C_1$–$C_8$-alkyl radical, or a benzyl or phenyl radical which is unsubstituted or halogen-, methyl-, $C_1$–$C_3$-alkoxy-, trifluoromethyl-, cyano- or nitro-substituted in the phenyl moiety.

Specifically, mention may be made, for example, of the following pyridine thioethers IIa of Tables 1–4, of the pyridine sulfoxides IIb of Table 5–8 and of the pyridine sulfones IIc of Tables 9–12.

Preference is given to the pyridine thioethers II.001–II.116 mentioned in Table 1 of Formula IIa1

TABLE 1

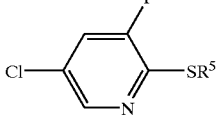

IIa1

TABLE 2

| No. | $R^2$ |
|---|---|
| IIa1.001 | $CH_3$ |
| IIa1.002 | $C_2H_5$ |
| IIa1.003 | n-$C_3H_7$ |
| IIa1.004 | i-$C_3H_7$ |
| IIa1.005 | n-$C_4H_9$ |
| IIa1.006 | sec-$C_4H_9$ |
| IIa1.007 | i-$C_4H_9$ |
| IIa1.008 | tert-$C_4H_9$ |
| IIa1.009 | n-$C_5H_{11}$ |
| IIa1.010 | sec-$C_5H_{11}$ |
| IIa1.011 | $CH_2$—$CH_2$—$CH(CH_3)_2$ |
| IIa1.012 | $CH_2$—$CH(CH_3)$—$CH_2$—$CH_3$ |
| IIa1.013 | $CH(CH_3)$—$CH(CH_3)_2$ |
| IIa1.014 | $CH(C_2H_5)_2$ |
| IIa1.015 | n-$C_6H_{13}$ |
| IIa1.016 | sec-$C_6H_{13}$ |
| IIa1.017 | $CH(C_2H_5)$-n-$C_3H_7$ |
| IIa1.018 | $CH(CH_3)$—$CH(CH_3)$—$C_2H_5$ |
| IIa1.019 | n-$C_7H_{15}$ |
| IIa1.020 | sec-$C_7$—$H_{15}$ |
| IIa1.021 | $CH(C_2H_5)$-n-$C_4H_9$ |
| IIa1.022 | $CH(CH_3)$—$CH(CH_3)$-n-$C_3H_7$ |
| IIa1.023 | n-$C_8H_{17}$ |
| IIa1.024 | sec-$C_8H_{17}$ |
| IIa1.025 | $CH(C_2H_5)$-n-$C_5H_{11}$ |
| IIa1.026 | n-$C_9H_{19}$ |
| IIa1.027 | sec-$C_9H_{19}$ |
| IIa1.028 | $CH(C_2H_5)$-n-$C_6H_{13}$ |
| IIa1.029 | n-$C_{10}H_{21}$ |
| IIa1.030 | sec-$C_{10}H_{21}$ |
| IIa1.031 | $CH_2$—$CH_2$—O—$CH_3$ |
| IIa1.032 | $CH_2$—$CH_2$—O—$C_2H_5$ |
| IIa1.033 | $CH_3$—$CH(OCH_3)$—$CH_3$ |
| IIa1.034 | $(CH_2)_3$—O—$CH_3$ |
| IIa1.035 | $(CH_2)_3$—O—$C_2H_5$ |
| IIa1.036 | $(CH_2)_4$—O—$CH_3$ |
| IIa1.037 | $CH_2CH_2Cl$ |
| IIa1.038 | $(CH_2)_3Cl$ |
| IIa1.039 | $(CH_2)_4Cl$ |
| IIa1.040 | cyclopropyl |
| IIa1.041 | cyclobutyl |
| IIa1.042 | cyclopentyl |
| IIa1.043 | cyclohexyl |
| IIa1.044 | cycloheptyl |
| IIa1.045 | cyclooctyl |
| IIa1.046 | $CH_2$=$CH_2$ |
| IIa1.047 | $CH_2$—CH=$CH_2$ |
| IIa1.048 | $CH_2CH$=CH—$CH_3$ |
| IIa1.049 | $CH(CH_3)$—CH=$CH_2$ |
| IIa1.050 | $CH_2$—$CH_2$—$C(CH_3)$=$CH_2$ |
| IIa1.051 | $CH_2CH$=$C(CH_3)_2$ |
| IIa1.052 | $C(CH_3)_2$—CH=$CH_2$ |
| IIa1.053 | $CH_2$—C≡CH |
| IIa1.054 | $CH_2$—C≡C—$CH_3$ |
| IIa1.055 | $CH(CH_3)$—C≡CH |
| IIa1.056 | $C(CH_3)_2$—C≡CH |

TABLE 2-continued

| No. | $R^2$ |
|---|---|
| IIa1.057 | C(C≡CH)—$CH(C_2H_5)$-n-$C_4H_9$ |
| IIa1.058 | $CH_2$—$CH_2$—CN |
| IIa1.059 | $(CH_2)_3CN$ |
| IIa1.060 | $CH_2CH_2NO_2$ |
| IIa1.061 | $(CH_2)_3NO_2$ |
| IIa1.062 | phenyl |
| IIa1.063 | 2-chlorophenyl |
| IIa1.064 | 3-chlorophenyl |
| IIa1.065 | 4-chlorophenyl |
| IIa1.066 | 2,3-dichlorophenyl |
| IIa1.067 | 2,4-dichlorophenyl |
| IIa1.068 | 2,5-dichlorophenyl |
| IIa1.069 | 2,6-dichlorophenyl |
| IIa1.070 | 2,4,6-trichlorophenyl |
| IIa1.071 | 2-tolyl |
| IIa1.072 | 3-tolyl |
| IIa1.073 | 4-tolyl |
| IIa1.074 | 2-chloro-4-tolyl |
| IIa1.075 | 2,6-dichloro-4-tolyl |
| IIa1.076 | 4-chloro-2-tolyl |
| IIa1.077 | 4,6-dichloro-2-tolyl |
| IIa1.078 | 2-methoxyphenyl |
| IIa1.079 | 3-methoxyphenyl |
| IIa1.080 | 4-methoxyphenyl |
| IIa1.081 | 2-chloro-4-methoxyphenyl |
| IIa1.082 | 2,6-dichloro-4-methoxyphenyl |
| IIa1.083 | 4-chloro-2-methoxyphenyl |
| IIa1.084 | 4,6-dichloro-2-methoxyphenyl |
| IIa1.085 | 2-nitrophenyl |
| IIa1.086 | 3-nitrophenyl |
| IIa1.087 | 4-nitrophenyl |
| IIa1.088 | 4-methyl-2-nitrophenyl |
| IIa1.089 | 4-chloro-2-nitrophenyl |
| IIa1.090 | 4-methoxy-2-nitrophenyl |
| IIa1.091 | 2-trifluoromethylphenyl |
| IIa1.092 | 3-trifluoromethylphenyl |
| IIa1.093 | 4-trifluoromethylphenyl |
| IIa1.094 | 2-chloro-4-trifluoromethylphenyl |
| IIa1.095 | 4-chloro-2-trifluoromethylphenyl |
| IIa1.096 | 2-cyanophenyl |
| IIa1.097 | 3-cyanophenyl |
| IIa1.098 | 4-cyanophenyl |
| IIa1.099 | 2-methyl-4-nitrophenyl |
| IIa1.100 | 5-methyl-2-nitrophenyl |
| IIa1.101 | 1-naphthyl |
| IIa1.102 | 2-naphthyl |
| IIa1.103 | 4-methyl-1-naphthyl |
| IIa1.104 | 4-chloro-1-naphthyl |
| IIa1.105 | benzyl |
| IIa1.106 | 2-methylbenzyl |
| IIa1.107 | 3-methylbenzyl |
| IIa1.108 | 4-methylbenzyl |
| IIa1.109 | 2-chlorobenzyl |
| IIa1.110 | 3-chlorobenzyl |
| IIa1.111 | 4-chlorobenzyl |
| IIa1.112 | 2,4-dichlorobenzyl |
| IIa1.113 | 2,4,6-trichlorobenzyl |
| IIa1.114 | 2-trifluoromethylbenzyl |
| IIa1.115 | 3-trifluoromethylbenzyl |
| IIa1.116 | 4-trifluoromethylbenzyl |

Furthermore, preference is given to the pyridine thioethers IIa2.001–IIa2.116 of the formula IIa2, which differ from the compounds IIa1.001–IIa1.116 in that in position 5 of the pyridine ring, a trifluoromethyl group replaces chlorine.

TABLE 3

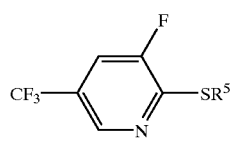
IIa2

Furthermore, preference is given to the pyridine thioethers IIa3.001–IIa3.116 of the formula IIa3, which differ from the compounds IIa1.001–IIa1.116 in that position 5 of the pyridine ring accommodates a methylsulfonyl group.

TABLE 4

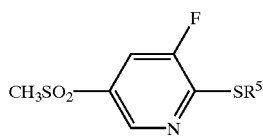
IIa3

Furthermore, preference is given to the pyridine thioethers IIa4.001–IIa4.116 of the formula IIa4, which differ from the compounds IIa1.001–IIa1.116 in that in position 5 of the pyridine ring a cyano group replaces chlorine.

TABLE 5

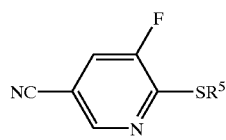
IIa4

Furthermore, preference is given to the thiopyridines IIb1.001–IIb1.116 of the formula IIb1, which differ from the compounds IIa1.001–IIa1.116 in that they are the corresponding sulfoxides.

TABLE 6

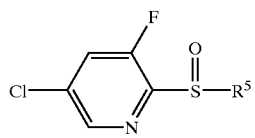
IIb1

Furthermore, preference is given to the thiopyridines IIb2.001–IIb2.116 of the formula IIb2, which differ from the compounds IIa2.001–IIa2.116 in that they are the corresponding sulfoxides.

TABLE 7

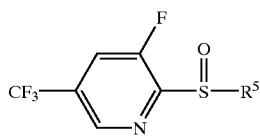
IIb2

Furthermore, preference is given to the thiopyridines IIb3.001–IIb3.116 of the formula IIb3, which differ from the compounds IIa3.001–IIa3.116 in that they are the corresponding sulfoxides.

TABLE 8

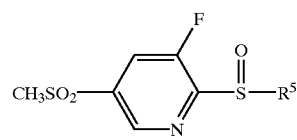
IIb3

Furthermore, preference is given to the thiopyridines IIb4.001–IIb4.116 of the formula IIb4, which differ from the compounds IIa4.001–IIa4.116 in that they are the corresponding sulfoxides.

TABLE 9

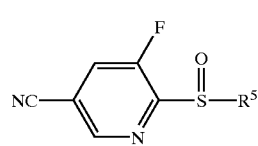
IIb4

Furthermore, preference is given to the thiopyridines IIc1.001–IIc1.116 of the formula IIc1, which differ from the compounds IIa1.001–IIa1.116 in that they are the corresponding sulfones.

TABLE 10

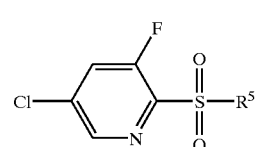
IIc1

Furthermore, preference is given to the thiopyridines IIc2.001–IIc2.116 of the formula IIc2, which differ from the compounds IIa2.001–IIa2.116 in that they are the corresponding sulfones.

TABLE 11

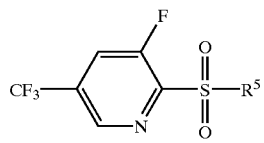
IIc2

Furthermore, preference is given to the thiopyridines IIc3.001–IIc3.116 of the formula IIc3, which differ from the compounds IIa3.001–IIa3.116 in that they are the corresponding sulfones.

TABLE 12

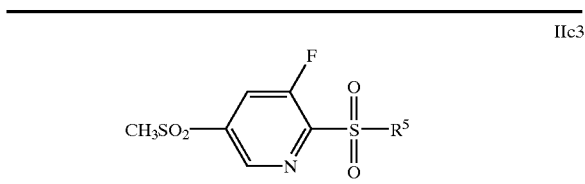

IIc3

Furthermore, preference is given to the thiopyridines IIc4.001–IIc4.116 of the formula IIc4, which differ from the compounds IIa4.001–IIa4.116 in that they are the corresponding sulfones.

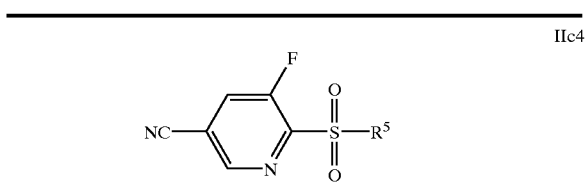

IIc4

If the compounds IIa–c are prepared using 2,3-difluoro-5-trifluoromethylpyridine and thiophenol as nucleophile and using hydrogen peroxide as oxidizing agent, the reaction can be illustrated by the following scheme:

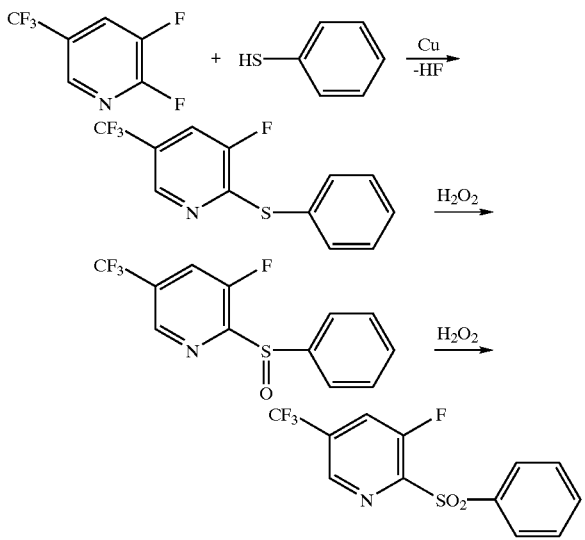

It is also possible to use peracetic acid, sodium hypochlorite or chlorine and bromine as oxidizing agents instead of hydrogen peroxide in processes analogous to the above scheme.

Preferred embodiments of the process are specified below.

The reaction of the 2-halopyridines V with a thiol VI is advantageously carried out in the presence of a solvent at 80–250° C., preferably 120–200° C., particularly preferably 140–180° C.

Solvents that are used for these reactions—depending on the temperature range—are hydrocarbons such as toluene and xylene, chlorinated hydrocarbons such as 1,2-dichloroethane, 1,1,2,2-tetrachloroethane, chlorobenzene, 1,2-, 1,3- or 1,4-dichlorobenzene, ethers such as 1,4-dioxane or anisol, glycol ethers such as dimethyl glycol ether, diethyl glycol ether or diethylene glycol dimethyl ether, esters such as ethyl acetate, propyl acetate, methyl isobutyrate or isobutyl acetate, carboxamides such as DMF or N-methylpyrrolidone, nitrated hydrocarbons such as nitrobenzene, ureas such as tetraethylurea, tetrabutylurea, dimethylethyleneurea and dimethylpropyleneurea, sulfoxides such as dimethyl sulfoxide, sulfones such as dimethyl sulfone, diethyl sulfone and tetramethylene sulfone, nitriles such as acetonitrile, propionitrile, butyronitrile or isobutyronitrile; water, or else mixtures of individual solvents.

The reaction is particularly preferably carried out in the melt without the use of a solvent.

The molar ratios in which the starting materials are reacted with each other are generally 0.9–1.4, preferably 0.95–1.1, particularly preferably 0.98–1.04, for the ratio of thiol to 2-halopyridine V. The concentration of the starting materials in the solvent is 0.1–5 mol/l, preferably 0.2–2 mol/l.

The reaction is promoted by the presence of a copper catalyst. Suitable catalysts are copper oxide, salts such as copper(II) chloride, copper sulfate, copper nitrate, copper acetate and copper carbonate. Particular preference is given to using finely distributed metallic copper, for example copper powder or copper bronze. The molar amount of catalyst, based on the 2-halopyridine V, is 0.001–10, preferably 0.001–1, particularly preferably 0.001–0.1 mol %.

The reaction can also be carried out in the presence of an organic base such as, for example, triethylamine, tri-n-propylamine, N-ethyldiisopropylamine, pyridine, $\alpha$-, $\beta$-, $\gamma$-picoline, 2,4-, 2,6-lutidine, N-methylpyrrolidine, triethylene diamine, dimethylaniline, N,N-dimethylcyclohexylamine, quinoline or acridine.

The reaction is preferably carried out under acidic conditions by flushing the hydrogen halide that is eliminated during the reaction out of the reaction mixture by means of an inert gas, for example nitrogen, or by letting it escape into a gas washer under autogenous pressure.

Advantageously, the 2-halopyridine V is added over a period of 10 to 60 min to a mixture of the thiol VI and the catalyst at 20–80° C., and the mixture is then stirred for another 0.5 to 12 hours, preferably 1 to 8 hours, at 140–180° C. to allow the reaction to go to completion.

However, it is also possible to add the thiol VI to a mixture of 2-halopyridine V and catalyst and then to complete the reaction as described above.

In the case of low-boiling 2-halopyridines V or thiols VI, the reaction can also be carried out in an autoclave.

If only one of the two starting materials has a low boiling point, the higher-boiling component can be initially charged together with the catalyst and the low-boiling component can be introduced directly at the reaction temperature of preferably 120–200° C., particularly preferably 140–180° C., or as a gas, at the rate of its consumption.

The reaction can be carried out under atmospheric or superatmospheric pressure, continuously or batchwise.

The oxidation of the pyridine thioethers of the formula IIa to the pyridine sulfoxides IIb and pyridine sulfones IIc is advantageously carried out with hydrogen peroxide, the pyridine sulfoxides IIb being obtained with approximately equivalent amounts of oxidant, and the pyridine sulfones IIc being obtained with approximately double the molar amount.

Examples of solvents which can be used include water, acetonitrile, carboxylic acids such as acetic acid, trifluoroacetic acid, propionic acid, alcohols such as methanol, ethanol, isopropanol, tert-butanol and chlorinated hydrocarbons such as methyl ethyl ketone. Water, methanol, acetic acid and trifluoroacetic acid are particularly preferred.

In a particularly preferred variant, the reaction can also be catalyzed by adding relatively strong acids such as trifluoroacetic acid or perchloric acid. However, suitable catalysts additionally include metal compounds, eg. transition metal oxides such as vanadium pentoxide, sodium tungstate, potassium dichromate, iron oxide tungstate, sodium tungstate/molybdic acid, osmic acid, titanium trichloride, selenium dioxide, phenylselenenic acid, vanadyl 2,4-pentanedionate.

The catalysts are generally employed in an amount of from 0.5 to 10%, but it is also possible to employ stoichiometric amounts because the inorganic catalysts can easily be filtered off and recovered.

Another preferred oxidizing agent is peracetic acid or hydrogen peroxide/acetic anhydride, possibly also the peracetic acid which is present in equilibrium in a hydrogen peroxide/acetic acid mixture.

Another preferred oxidizing agent is pertrifluoroacetic acid or the hydrogen peroxide/trifluoroacetic acid mixture or else the hydrogen peroxide/trifluoroacetic anhydride mixture.

Oxidation with hydrogen peroxide in glacial acetic acid is generally very selective, but frequently slow. The reaction time can generally be reduced by adding trifluoroacetic acid. The oxidation with hydrogen peroxide in pure trifluoroacetic acid frequently leads to the formation of the corresponding N-oxides, as described for example in Chimia 29 (1975), 466. A rapid and selective oxidation of the pyridine thioethers IIa to the corresponding sulfoxides IIb and sulfones IIc is possible using solutions of hydrogen peroxide in mixtures of acetic acid and trifluoroacetic acid in the ratio of 10:1 to 1:1, in particular 6:1 to 4:1, by volume. Therefore, particular preference is given to using these mixtures as solvent.

It is possible furthermore to use as solvent petroleum ether, the abovementioned solvents and the abovementioned catalysts.

Besides peracetic acid and pertrifluoroacetic acid, it is also possible to employ perbenzoic acid, monoperphthalic acid or 3-chloroperbenzoic acid, expediently in chlorinated hydrocarbons such as methylene chloride or 1,2-dichloroethane.

Also very suitable for oxidizing the thiols to sulfoxides or sulfones are chlorine and bromine. Favorable solvents are water, acetonitrile, dioxane, two-phase systems such as aqueous potassium bicarbonate solution/dichloromethane, and, in the case of pyridine alkyl thioethers, also acetic acid.

It is furthermore possible to employ as source of active halogen tert-butyl hypochlorite, hypochlorous and hypobromous acids, their salts, also N-halo compounds such as N-bromo- and N-chlorosuccinimide or else sulfuryl chloride.

Also favorable for the oxidation are dinitrogen tetroxide, eg. in the technically simple variant with air/nitrogen dioxide or trioxide and, for example, osmium(VIII) oxide as catalyst. The oxidation can also be carried out directly with nitric acid, in which case suitable additional solvents are acetic anhydride and acetic acid, and suitable catalysts are copper(I) and (II) bromide and chloride.

Also suitable for the oxidation is photosensitized oxygen transfer, in which case recommended photosensitizers are chlorophyll, protoporphyrin, Rose Bengal or Methylene Blue. Suitable inert solvents are hydrocarbons such as pentane, hexane, heptane, cyclohexane, chlorinated hydrocarbons such as methylene chloride, 1,2-dichloroethane, 1,1,2,2-tetrachloroethane, alcohols such as methanol, ethanol, n-propanol or isopropanol, ketones such as acetone, methyl ethyl ketone, polar aprotic solvents such as acetonitrile, propionitrile or aromatic hydrocarbons such as benzene, toluene, chlorobenzene or xylene. In place of oxygen, it is also possible to use ozone in the abovementioned solvents, plus ether, 1,4-dioxane or THF.

Besides photosensitization, catalysts can also be recommended for oxidation with oxygen, eg. oxides and sulfides of nickel, copper, aluminum, tungsten, chromium, vanadium, ruthenium, titanium, manganese, molybdenum, magnesium and iron.

Either pyridine sulfoxides IIb or their pyridine sulfones IIc are obtained depending on the stoichiometry of the oxidizing agents used. The molar ratios in which the starting materials are reacted with each other are generally 0.9–1.8, preferably 1.05–1.3, for the ratio of pyridine thioether IIa to oxidizing agent in the case of oxidation to pyridine sulfoxide IIb and generally 1.9–3.5, preferably 2.05–2.9, in the case of oxidation to pyridine sulfone IIC.

The concentration of the starting materials in the solvent is generally 0.1–5 mol/l, preferably 0.2–2 mol/l.

It is advantageous to introduce the pyridine thioether or the pyridine sulfoxide, if appropriate with one of the abovementioned catalysts, into one of the abovementioned solvents and then to add the oxidizing agent over the course of 0.25–20 hours with stirring. The addition and reaction temperatures depend on the optimum efficiency of the oxidizing agents in question and the suppression of side reactions. If photosensitized oxygen is used, the reaction is generally carried out at −20 to 80° C., but in the case of metal catalysis, the reaction is generally carried out at 50 to 140° C., and if ozone is used, the reaction is generally carried out at −78 to 60° C. Owing to the limited solubility of the oxygen derivatives, they have to be introduced continuously over a prolonged period of time (up to 20 hours) into the reaction mixture until the oxidation has ended at the sulfoxide or sulfone stage. If air/nitrogen dioxide or trioxide are used, the reaction is preferably carried out at 15–150° C. over a period of 1–15 hours. Liquid or easily soluble oxidizing agents such as hydrogen peroxide, the peracetic acid and pertrifluoroacetic acid which are formed together with acetic anhydride or in equilibrium with acetic acid and trifluoroacetic acid, respectively, hypochlorous or hypobromous acid, tert-butyl hypochlorite, chlorine or bromine, N-chlorosuccinimide or N-bromosuccinimide or nitric acid can be added over shorter periods of time of 0.25–6 hours to the reaction mixture of the pyridine thioether or sulfoxide, depending on the exothermic character of the reaction, to end the reaction after a further 1–60 hours. Moreover, preference is given to adding the liquid or dissolved oxidizing agent in portions. If hydrogen peroxide and peracetic acid or pertrifluoroacetic acid are used, the reaction is generally carried out at 0–90° C., if tert-butyl hypochlorite is used, the reaction is generally carried out at −78 to 30° C., if N-halogen compounds are used, the reaction is usually carried out at 0–30° C., and if nitric acid is used, the reaction is usually carried out at 20 to 140° C. If chlorine or bromine is used, a reaction temperature of 0–40° C. is recommended.

The oxidations can be carried out under atmospheric or superatmospheric pressure, continuously or batchwise.

Advantageously, the multi-step reaction can also be carried out as a one-pot reaction, by reacting the thioethers IIa which are obtained in the first step of the synthesis in the reaction of the 2-halopyridines V with the thiols VI without isolation and purification directly to give the sulfoxides IIb or the sulfones IIc. Thus, if appropriate, the reaction product IIa is allowed to cool to 90–120° C., a solvent, for example trifluoroacetic acid, preferably acetic acid and/or water, is added, if appropriate, and the oxidizing agent is then added at the rate of its consumption. Preferred oxidizing agents are hydrogen peroxide and especially sodium hypochlorite.

For work-up, the intermediates IIa–c are taken up in a water-imiscible solvent, acidic impurities and/or oxidizing agents are extracted using dilute bases or water, the solution is dried and the solvent is removed under reduced pressure.

The substituted 2-phenylpyridines I are usually preparable by one of the abovementioned processes. However, for economical or technical reasons it may be more advantageous to prepare some of the compounds I from similar 2-phenylpyridines which differ in the meaning of one radical.

Work-up of the reaction mixtures is usually carried out by methods known per se, for example by diluting the reaction solution with water and subsequently isolating the product by filtration, crystallization or solvent extraction, or by removing the solvent, partitioning the residue in a mixture of water and a suitable organic solvent and work-up of the organic phase to afford the product.

The substituted 2-phenylpyridines of the formula I may contain one or more chiral centers, in which case they are usually obtained as enantiomer or diastereomer mixtures. If desired, these mixtures can be separated into substantially pure isomers using the customary methods for this purpose, such as crystallization or chromatography, including chromatography over an optically active adsorbate. Pure optically active isomers can also be prepared, for example, from suitable optically active starting materials.

Those substituted 2-phenylpyridines I where $R^6$, $R^7$ and $R^9$=hydrogen can be converted in a manner known per se into their salts, preferably into their alkali metal salts.

Salts of I where the metal ion is not an alkali metal ion can be prepared by cation exchange of the corresponding alkali metal salt in a conventional manner, similarly ammonium, phosphonium, sulfonium and sulfoxonium salts by means of ammonia, phosphonium, sulfonium or sulfoxonium hydroxides.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds I may also be used in crops which tolerate the action of herbicides owing to breeding, including genetic engineering methods.

Moreover, the substituted 2-phenylpyridines I are also suitable for the desiccation and/or defoliation of plants.

As desiccants, they are suitable, in particular, for desiccating the aerial parts of crop plants such as potatoes, oilseed rape, sunflowers and soybeans. This allows completely mechanical harvesting of these important crop plants.

Also of economic interest is the facilitation of harvesting, which can be achieved by concentrating into a short period of time fruit drop, or reduction of the adherence to the tree, in citrus fruit, olives or other species and varieties of pomaceous fruit, stone fruit and nuts. The same mechanism, i.e. promotion of the formation of abscission tissue between fruit or leaf and shoot of the plant, is also important for readily controllable defoliation of useful plants, in particular cotton.

Moreover, shortening the period within which the individual cotton plants mature results in improved fiber quality after harvesting.

The compounds I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

Suitable as inert auxiliaries are essentially the following: mineral oil fractions of medium to high boiling point, such as kerosene and diesel oil, furthermore coaltar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 2-phenylpyridines I, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the active ingredients I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum). The compounds I according to the invention can be formulated for example as follows:

I 20 parts by weight of the active ingredient of Example No. 9 are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II 20 parts by weight of the active ingredient of Example No. 8 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III 20 parts by weight of the active ingredient of Example No. 6 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV 20 parts by weight of the active ingredient of Example No. 9 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of the active ingredient of Example No. 14 are mixed with 97 parts by weight of finely divided kaolin. This gives a dust which comprises 3% by weight of active ingredient.

VI 20 parts by weight of the active ingredient of Example No. 8 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the active ingredient of Example No. 6 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active ingredient No. 14 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The herbicidal compositions or the active ingredients can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of active ingredient are from 0.0005 to 3.0, preferably 0.0005 to 1.0, kg/ha of active substance (a.s.), depending on the control target, the season, the target plants and the growth stage.

To widen the spectrum of action and to achieve synergistic effects, the 2-phenylpyridines I may be mixed with a large number of representatives of other herbicidal or growth-regulating active ingredients and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

PREPARATION OF THE INTERMEDIATES II

EXAMPLE 1

3-Fluoro-2-phenylthio-5-trifluoromethylpyridine

Over a period of 2.5 h, 59.6 g (0.326 mol) of 2,3-difluoro-5-trifluoromethylpyridine were added at 148–156° C. to 37.7 g (0.338 mol) of 98.7% pure thiophenol and 2.1 mg (0.01 mol %) of copper powder, and the mixture was stirred at 156–164° C. for 2 hours. After cooling, the residue was taken up in methylene chloride, washed with 0.5 N of aqueous sodium hydroxide solution and with water, dried over magnesium sulfate and concentrated under reduced pressure. 88.9 g (100% of theory) of the title compound of n24/D=1.5539 were obtained.

EXAMPLE 2

5-Chloro-3-fluoro-2-phenylthio-pyridine

Starting from 93 g (0.508 mol) of 2,3-difluoro-5-chloropyridine, 58.8 g (0.5276 mol) of 98.7% pure thiophenol and 3.2 mg (0.01 mol %) of copper powder, 121.5 g (99.9% of theory) of the title compound were obtained as a colorless oil after 1.5 h of stirring in a pressure apparatus at 185° C. and work-up by the method of Example 1. 1H NMR (ppm, $d_6$-DMSO) 8.35 (s/1H), 8.05 (d/1H), 7.4–7.6 (m/5H).

EXAMPLE 3

3-Fluoro-3-phenylsulfinyl-5-trifluoromethylpyridine 20 g (0.0693 mol) of 95% pure 3-fluoro-2-phenylthio-5-trifluoromethylpyridine were initially charged in 100 ml of glacial acetic acid and 20 ml of trifluoroacetic acid and admixed with stirring at 22° C. over a period of 5 minutes with 5.64 g (0.083 mol) of 50% strength hydrogen peroxide, and stirred at 22° C. for 10 h. The reaction mixture was poured into 1 l of ice-water and extracted with methylene chloride, and the organic phase was washed with saturated sodium bicarbonate solution and with water. After drying, filtration through silica gel and concentration under reduced pressure, 19.1 g (95.4% of theory) of the title compound of n24/D=1.5522 were obtained.

EXAMPLE 4

3-Fluoro-2-phenylsulfonyl-5-trifluoromethylpyridine

In 4 portions, 63.2 g (0.1145 mol) of 13.5% strength sodium hypochlorite were added in each case over a period of 10 min with stirring at 25–30° C. to a mixture of 13.6 g (0.0498 mol) of the compound of Example 5 in 85 ml of water and 60 ml of glacial acetic acid, and the mixture was stirred for a total of 2.5 h. The reaction mixture was poured into 1 l of ice-water and extracted with methylene chloride, and the organic phase was washed with saturated sodium bicarbonate solution and with water. Drying and concentration under reduced pressure yielded 15.1 g (98.9% of theory) of the title compound of mp. 82–83° C.

EXAMPLE 5

5-Chloro-3-fluoro-2-phenylsulfinylpyridine

Over a period of 15 minutes, 33.8 g (0.497 mol) of 50% strength hydrogen peroxide were added with stirring at 23–28° C. to a solution of 119 g (0.497 mol) of the compound of Example 6 in 500 ml of glacial acetic acid and 150 ml of trifluoroacetic acid, and the mixture was stirred at 23° C. for 14 h. The reaction mixture was poured into 2 l of ice-water and extracted with methylene chloride, and the organic phase was washed with saturated sodium bicarbonate solution and with water. Concentration gave 123.5 g (97.3% of theory) of the title compound as colorless crystals. These were stirred with ether/pentane 2:8, after which 116.1 g (91.6% of theory) of mp. 77–78° C. remained.

PREPARATION OF THE PHENYLPYRIDINES I

EXAMPLE 6

3-Fluoro-2-(4-chloro-2-fluoro-5-methoxyphenyl)-5-trifluoromethylpyridine [Table 1, Ia. 1]

A Grignard solution, prepared from 16.96 g (0.0708 mol) of 1-bromo-4-chloro-2-fluoro-5-methoxybenzene and 1.98 g (0.0813 mol) of magnesium turnings in 60 ml of THF was added with stirring and gentle cooling at 24–36° C. to a solution of 17.8 g (0.0616 mol) of 3-fluoro-2-phenylsulfinyl1-5-trifluoromethylpyridine in 45 ml of THF over a period of 20 min. The reaction mixture was stirred at 24° C. for 4 h and then concentrated under reduced pressure, taken up in methylene chloride and extracted in succession with 1 N hydrochloric acid, 1 N of aqueous sodium hydroxide solution and with water and then concentrated. The residue was stirred in 1 N of aqueous sodium hydroxide solution for 45 min at 95° C. and then concentrated to a quarter of its volume at 300 mbar. The residue was partitioned between methylene chloride and water and the organic phase was dried, filtered off with suction through silica gel and concentrated under reduced pressure. 8.7 g (43.7% of theory) of the title compound of mp. 79–80° C. were obtained.

EXAMPLE 7

2-Chloro-4-fluoro-5-(3-fluoro-5-trifluoromethylpyridin-2-yl)phenol [Table 1, Ia. 249]

8.5 g (0.0263 mol) of 3-fluoro-2-(4-chloro-2-fluoro-5-methoxyphenyl)-5-trifluoromethylpyridine were added with stirring to 110 ml of 47% strength hydrobromic acid, and the mixture was refluxed for 2 h. After cooling, the clear solution was poured into 500 ml of water and extracted with methylene chloride. The organic phase was extracted with 1 N sodium hydroxide solution and the extract was acidified and extracted with ethyl acetate. Drying and concentration yielded 6.7 g (82.1% of theory) of the title compound of mp. 94–96° C.

EXAMPLE 8

Methyl (R)-2-(2-chloro-4-fluoro-5-(3-fluoro-5-trifluoromethylpyridin-2-yl)phenoxy)propionate (Table 1, Ia. 54)

A mixture of 0.62 g (0.002 mol) of the compound of Example 7, 0.29 g (0.0024 mol) of methyl S-(-)-2-chloropropionate and 0.55 g (0.004 mol) of potassium carbonate powder in 20 ml of DMF was stirred at 60–70° C., for 1.5 h, with HPLC monitoring. After cooling, 100 ml of water were added and the mixture was extracted 3 times with methyl tert-butyl ether. The organic phase was dried, filtered through silica gel and concentrated under reduced pressure.

0.78 g (98.6% of theory) of the title compound were obtained as a viscous resin. NMR (360 MHz, CDCl$_3$): 7.75 d/1 (Pyr), 8.8 s/1 (Pyr), 7.18 d/1 (Ph), 7.25 m/1 (Ph), 4.8 q/1 (CH), 3.75 s/3 (O—CH$_3$), 1.7 d/3 (CH$_3$). After the addition of TFAE shift reagent, the enantiomer ratio was R:S=93:7.

EXAMPLE 9

Isobutyl (R)-2-(2-chloro-4-fluoro-5-(3-fluoro-5-trifluoromethylpyridin-2-yl)phenoxy)propionate [Table 1, Ia. 265]

By the method of Example 8 and starting from 4.7 g (0.0152 mol) of the compound of Example 7, 3.0 g (0.0182 mol) of isobutyl L-chloropropionate and 4.2 g (0.03 mol) of potassium carbonate powder, 6.5 g (97.8% of theory) of the title compound of n24/D=1.5061 were obtained.

EXAMPLE 10

(R)-2-(2-Chloro-4-fluoro-5-(3-fluoro-5-trifluoromethylpyridin-2-yl)phenoxy)propionic Acid [Table 1, Ia. 261]

2.0 g (0.0046 mol) of the compound of Example 9 were stirred at 80° C. in a mixture of 35 ml of glacial acetic acid and 15 ml of 2 N hydrochloric acid for 3 h. After cooling, the mixture was partitioned between methylene chloride and water and the organic phase was dried and concentrated. 1.6 g (91.7% of theory) of the title compound of mp. 48–50° C. were obtained.

EXAMPLE 11

R-2-(2-Chloro-4-fluoro-5-(3-fluoro-5-trifluoromethyl)pyridin-2-yl)phenoxy)propionyl Chloride 1.0 g (0.0026 mol) of the compound of Example 10 and 0.5 g (0.0042 mol) of thionyl chloride in 10 ml of 1,2-dichloroethane was stirred at 83° C. for 2 h. The reaction mixture was then concentrated, yielding 1.0 g (95.4% of theory) of the title compound as a colorless oil.

EXAMPLE 12

Propargyl (R)-2-(2-chloro-4-fluoro-5-(3-fluoro-5-trifluoromethylpyridin-2-yl)phenoxy)propionate [Table 1, Ia. 266]

A mixture of 0.13 g (0.0013 mol) of triethylamine and 1 ml of propargyl alcohol was added at 20–29° C. with stirring to a solution of 0.5 g (0.00125 mol) of the compound of Example 11 in 10 ml of 1,2-dichloroethane, and the mixture was stirred at 23° C. for 1 h. The reaction mixture was partitioned between methylene chloride and water and the organic phase was dried. Concentration under reduced pressure gave 0.5 g (95.3% of theory) of the title compound as a colorless resin.

$^1$H NMR (270 MHz, CDCl$_3$) 7.75 d/1 (Pyr), 8.8 s/1 (Pyr), 7.18 d/1 (Ph), 7.25 m/1 (Ph), 4.85 q/1 (CH), 4.75 d/2 (CH$_2$), 2.4 m/1 (CH), 1.7 d/3 (CH$_3$).

EXAMPLE 13

2-Chloro-4-fluoro-5-(3-fluoro-5-trifluoromethylpyridin-2-yl)phenyl Propargyl Ether [Table 1, Ia. 5]

A mixture of 0.25 g (0.808 mmol) of the compound of Example 7, 0.12 g (0.97 mmol) of propargyl bromide and 0.22 g (1.62 mmol) of potassium carbonate powder in 10 ml of DMF was stirred for 2 h at 65–70° C. After cooling, 50 ml of water were added and the mixture was extracted 3 times with methyl tert-butyl ether, and the extracts were dried and concentrated, affording 0.28 g (100% of theory) of the title compound of mp. 68–70° C.

EXAMPLE 14

5-Chloro-3-fluoro-2-(4-chloro-2-fluoro-5-methoxyphenyl)pyridine [Table 1, Ia. 63]

A Grignard solution of 12.9 g (0.049 mol) of 4-chloro-2-fluoro-5-methoxyphenylmagnesium bromide in 60 ml of THF was added with stirring at 23–30° C. to a solution of 10 g (0.0392 mol) of 5-chloro-3-fluoro-2-phenylsulfinylpyridine in 150 ml of THF over a period of 10 min, and the mixture was stirred at 23° C. for another 4 h. The reaction mixture was concentrated under reduced pressure, taken up in methylene chloride and extracted in succession with 1 N hydrochloric acid, 1 N of aqueous sodium hydroxide solution and with water, and dried. The solution was filtered with suction through silica gel, concentrated, stirred with pentane, filtered off with suction and dried, affording 5.7 g (50.1% of theory) of the title compound of mp. 120–122° C.

Use Examples (Herbicidal Activity)

The herbicidal activity of the 2-phenylpyridines of the formula I was demonstrated by the following greenhouse experiments:

The culture containers used were plastic pots containing loamy sand with approximately 3.0% of humus as substrate. The seeds of the test plants were sown separately for each species.

For the pre-emergence treatment, the active ingredient, which had been suspended or emulsified in water, were applied directly after sowing by means of finely distributing nozzles. The containers were irrigated a little to promote germination and growth and subsequently covered with translucent plastic hoods until the plants had rooted. This cover caused uniform germination of the test plants, unless this was adversely affected by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 1.9 or 0.9 g/ha of a. S. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Abbreviation | Scientific name | Common name |
|---|---|---|
| ORYSA | *Oryza sativa* | rice |
| CHEAL | *Chenopodium album* | lambsquarters (goosefoot) |
| GALAP | *Galium aparine* | catchweed bedstraw |
| POLPE | *Polygonum persicaria* | ladysthumb |
| SETFA | *Setaria faberii* | giant foxtail |
| SETVI | *Setaria viridis* | green foxtail |
| SINAL | *Sinapis alba* | white mustard |

The Examples 8 and 9 according to the invention listed in Table C were compared with the corresponding compounds of WO 95/02580.

TABLE C

Comparison of compounds to determine the post-emergence herbicidal activity in greenhouse experiments

| | according to the invention | WO 95/02580 |
|---|---|---|
| Ex. No. | 8 (Ia.54 from Tab. 1) | A (I.516 from Tab. 4) |
| $R^1$ | F | Cl |
| $R^2$ | $CH_3$ | $CH_3$ |
| Ex. No. | 9 (Ia.265 from Tab. 1) | B |
| $R^1$ | F | Cl |
| $R^2$ | $CH_2CH(CH_3)CH_3$ | $CH_2CH(CH_3)CH_3$ |

The comparison showed a significantly higher herbicidal activity of the compounds according to the invention in combination with better crop safety, for example in rice.

Use Examples (Desiccant/defoliant Activity)

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to run off point with aqueous preparations of the active compounds (with an addition of 0.15% by weight of the fatty alcohol alkoxide Plurafac® LF 700, based on the spray mixture). The amount of water applied was 1000l/ha (converted). After 13 days, the number of leaves shed and the degree of defoliation in % were determined.

No leaves were shed in the untreated control plants.

We claim:

1. Substituted 2-phenylpyridines of the formula I

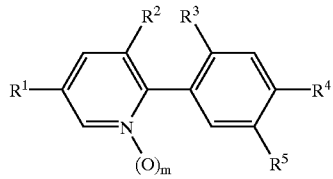

in which the substituents and the index m have the following meanings:

m is 0 or 1;

$R^1$ is halogen, $C_1$–$C_4$-haloalkyl, $C_1$–$C_4$-haloalkoxy, $C_1$–$C_4$-alkylthio, $C_1$–$C_4$-alkylsulfinyl, $C_1$–$C_4$-alkylsulfonyl, $C_1$–$C_4$-haloalkylthio or cyano;

$R^2$ is fluorine;

$R^3$ is hydrogen or halogen;

$R^4$ is halogen or cyano;

$R^5$ is $CO_2R^6$, $OR^7$, $SR^7$, $C(R^8)=N-O-R^7$ or $C(R^8)=C(R^8)-CO-O-R^6$, where $R^6$ is hydrogen, an unsubstituted or halogen-substituted $C_1$–$C_8$-alkyl-, $C_3$–$C_6$-alkenyl- or $C_3$–$C_6$-alkynyl radical; $C_1$–$C_4$-alkoxy-$C_1$–$C_4$-alkyl, $C_1$–$C_6$-alkoxycarbonyl-$C_1$–$C_4$-alkyl, $C_3$–$C_4$-alkenyloxycarbonyl-$C_1$–$C_4$-alkyl, $C_3$–$C_4$-alkynyloxycarbonyl-$C_1$–$C_4$-alkyl or $C_1$–$C_4$-alkoxy-($C_1$–$C_4$-alkoxy)carbonyl-$C_1$–$C_4$-alkyl;

$R^7$ may have the meaning of $R^6$ or may be $CH_2$—$CO_2$[$C_1$–$C_4$-alkylene]—$CO_2R^9$ or $CH$[$C_1$–$C_4$-alkyl]—$CO_2$—[$C_1$–$C_4$-alkylene]—$CO_2R^9$;

$R^8$ is hydrogen, halogen or $C_1$–$C_4$-alkyl and $R^9$ is hydrogen or $C_1$–$C_4$-alkyl, and the agriculturally useful salts of the compounds I.

2. Substituted 2-phenylpyridines of the formula I as claimed in claim 1, where the substituents and the index m have the following meanings:

m is 0, $R^1$ is $C_1$–$C_3$-fluoroalkyl, chlorine, methylsulfonyl or cyano;

$R^2$ is fluorine;

$R^3$ is fluorine or chlorine;

$R^4$ is chlorine;

$R^5$ is $CO_2R^6$, $OR^7$ or $SR^7$, where $R^6$ is hydrogen, $C_1$–$C_5$-alkyl, $C_3$–$C_4$-alkenyl, 3-chloroprop-2-ene, $C_3$–$C_4$-alkynyl, $C_1$–$C_3$-alkoxy-$C_1$–$C_2$-alkyl, $C_1$–$C_6$-alkoxycarbonyl-$C_1$–$C_2$-alkyl, propargyloxycarbonyl-$C_1$–$C_2$-alkyl, $C_1$–$C_3$-alkoxy-$C_1$–$C_3$-alkoxycarbonyl-$C_1$–$C_2$-alkyl;

$R^7$ may have the meaning of $R^6$ or may be $CH_2$—$CO_2$[$C_1$–$C_2$-alkylene]—$CO_2R^9$ or $CH$[$C_1$–$C_2$-alkyl]—$CO_2$—[$C_1$–$C_2$-alkylene]—$CO_2R^9$;

$R^8$ is hydrogen, halogen or $C_1$–$C_4$-alkyl and $R^9$ is hydrogen or $C_1$–$C_4$-alkyl, and the agriculturally useful salts of the compounds I.

3. A process for preparing substituted 2-phenylpyridines of the formula I as claimed in claim 1, which comprises reacting substituted pyridines of the formula II

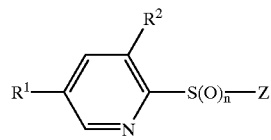

in which $R^1$ and $R^2$ are each as defined in claim 1, n is 1 or 2 and

Z is an aliphatic radical or an aryl radical, with an aryl compound of the formula III or IV

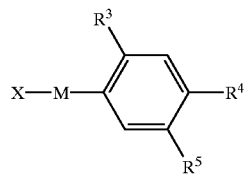

III M = Mg
IV M = Zn in which X is halogen and $R^3$, $R^4$ and $R^5$ are each as defined in claim 1.

4. Substituted thiopyridines of the general formula II

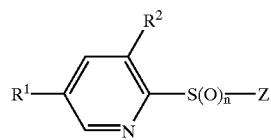

in which n is 0, 1 or 2;

$R^1$ is $C_1$–$C_3$-fluoroalkyl, chlorine, methylsulfonyl or cyano;

$R^2$ is fluorine and

Z is an unsubstituted or halogen-, $C_1$–$C_4$-alkoxy-, $C_1$–$C_4$-hydroxyalkyl-, $C_1$–$C_4$-alkoxycarbonyl-, di-($C_1$–$C_4$-alkylamino)carbonyl-, cyano- or nitro-substituted $C_1$–$C_{10}$-alkyl, $C_2$–$C_{10}$-alkenyl or $C_2$–$C_{10}$-alkynyl radical, a $C_3$–$C_8$-cycloalkyl radical or a $C_1$–$C_4$-alkylenephenyl, phenyl or naphthyl which is unsubstituted or halogen-, $C_1$–$C_3$-alkyl-, $C_1$–$C_3$-alkoxy-, trifluoromethyl-, cyano- or nitro-substituted in the phenyl or naphthyl moiety.

5. Substituted thiopyridines of the general formula II as claimed in claim 4, in which n is 1 or 2;

$R^1$ is trifluoromethyl, chlorine, methylsulfonyl or cyano;

$R^2$ is fluorine and

Z is an unsubstituted or chlorine- or methoxy-substituted $C_1$–$C_8$-alkyl radical, or a benzyl or phenyl radical which is unsubstituted or halogen-, methyl-, $C_1$–$C_3$-alkoxy, trifluoromethyl, cyano- or nitro-substituted in the phenyl moiety.

6. A herbicide comprising a herbicidally effective amount of at least one substituted 2-phenylpyridine of the formula I or an agriculturally useful salt of I as claimed in claim 1 and at least one inert liquid and/or solid carrier and, if desired, at least one adjuvant.

7. A composition for the desiccation and/or defoliation of plants, comprising amount sufficient to produce a desiccant and/or defoliant action of at least one substituted 2-phenylpyridine of the formula I or an agriculturally useful salt of I as claimed in claim 1 and at least one inert liquid and/or solid carrier and, if desired, at least one adjuvant.

8. A method for controlling undesirable vegetation, which comprises allowing a herbicidally effective amount of at least one substituted 2-phenylpyridine of the formula I or an agriculturally useful salt of I as claimed in claim 1 to act on plants, on their habitat or on seeds.

9. A method for the desiccation and/or defoliation of plants, which comprises allowing an amount sufficient to produce a desiccant and/or defoliant action of at least one substituted 2-phenylpyridine of the formula I or an agriculturally useful salt of I as claimed in claim 1 to act on plants.

\* \* \* \* \*